(12) United States Patent
Ploss et al.

(10) Patent No.: US 8,940,960 B2
(45) Date of Patent: Jan. 27, 2015

(54) HCV ENTRY FACTOR, OCCLUDIN

(75) Inventors: Alexander Ploss, New York, NY (US);
Matthew Evans, New York, NY (US);
Charles Rice, New York, NY (US)

(73) Assignee: The Rockefeller University, New York, NY (US)

( * ) Notice: Subject to any disclaimer, the term of this patent is extended or adjusted under 35 U.S.C. 154(b) by 303 days.

(21) Appl. No.: 13/122,339

(22) PCT Filed: Oct. 1, 2009

(86) PCT No.: PCT/US2009/059285
§ 371 (c)(1),
(2), (4) Date: Jun. 20, 2011

(87) PCT Pub. No.: WO2010/040001
PCT Pub. Date: Apr. 8, 2010

(65) Prior Publication Data
US 2011/0271356 A1    Nov. 3, 2011

Related U.S. Application Data

(60) Provisional application No. 61/102,588, filed on Oct. 3, 2008, provisional application No. 61/142,262, filed on Jan. 2, 2009.

(51) Int. Cl.
*C12N 15/90* (2006.01)
*C12N 15/63* (2006.01)

(52) U.S. Cl.
USPC ............ 800/18; 435/353; 435/354; 536/23.5; 800/9

(58) Field of Classification Search
CPC ............... C12N 15/90; A01K 67/0275; A01K 2267/0337; A01K 2217/00; A01K 49/0008
See application file for complete search history.

(56) References Cited

U.S. PATENT DOCUMENTS

| | | | |
|---|---|---|---|
| 6,110,747 A | 8/2000 | Blaschuk et al. | |
| 6,252,045 B1 | 6/2001 | Anderson et al. | |
| 6,559,286 B1 | 5/2003 | Tsukita | |
| 2002/0082391 A1 | 6/2002 | Anderson et al. | |

FOREIGN PATENT DOCUMENTS

| | | |
|---|---|---|
| JP | 2000-032984 A | 2/2000 |
| WO | 2007130646 | 11/2007 |
| WO | 2010040001 A1 | 4/2010 |

OTHER PUBLICATIONS

Benedicto et al, Hepatitis C Virus Envelope Components Alter Localization of Hepatocyte Tight Junction—Associated Proteins and Promote Occludin Retention in the Endoplasmic Reticulum, vol. 48 (4) pp. 1044-1053, Article first published online: Sep. 18, 2008.*

Feldman et al, Occludin: Structure, function and regulation, Advanced Drug Delivery Reviews 57 (2005) 883-917.*
Smith. Gene Transfer in Higher Animals: Theoretical Considerations and Key Concepts. J. Biotech. 2002, vol. 99, pp. 1-22.*
Ristevski et al, Making Better Transgenic Models: Conditional, Temporal, and Spatial Approaches, Molecular Biotechnology, 2005, pp. 153-163.*
Nusrat et al., "Multiple Protein Interactions Involving Proposed Extracellular Loop Domains of the Tight Junction Protein Occludin", Molecular Biology of the Cell, Apr. 2005, pp. 1725-1734, vol. 16.
Tavelin et al., "A New Principle for Tight Junction Modulation Based on Occludin Peptides", Molecular Pharmacology, 2003, pp. 1530-1540, vol./No. 64(6).
Tokunaga et al., "A Novel Monoclonal Antibody Against the Second Extracellular Loop of Occludin Disrupts Epithelial Cell Polarity", Journal of Histochemistry & Cytochemistry, 2007, pp. 735-744, vol./No. 55(7).
Trinkle-Mulcahy et al., "Identifying Specific Protein Interaction Partners Using Quantitative Mass Spectrometry and Bead Proteomes", J. Cell. Biol., Oct. 20, 2008, pp. 223-239, vol./No. 183(2).
Benedicto et al., "Hepatitis C Virus Envelope Components Alter Localization of Hepatocyte Tight Junction-Associated Proteins and Promote Occludin Retention in the Endoplasmic Reticulum", Hepatology, Sep. 18, 2008, pp. 1044-1053, vol. 48, No. 4.
Liu et al., "Tight Junction Proteins Claudin-1 and Occludin Control Hepatitis C Virus Entry and are Downregulated During Infection to Prevent Superinfection", Journal of Virology, Feb. 2009, pp. 2011-2014, vol. 83, No. 4.
Ploss et al., "Human Occludin is a Hepatitis C Virus Entry Factor Required for Infection of Mouse Cells", Nature, Feb. 12, 2009, pp. 882-886, vol. 457, No. 7231.
Brazzoli et al., "CD81 is a Central Regulator of Cellular Events Reuired for Hepatits C Virus Infection of Human Hepatocytes", Journal of Virology, Sep. 2008, pp. 8316-8329, vol. 82, No. 17.
Catanese et al., "High-Avidity Monoclonal Antibodies Against the Human Scavenger Class B Tyhpe I Receptor Efficiently Block Hepatitis C Virus Infection in the Presence of High-Density Lipoprotein", Journal of Virology, Aug. 2007, pp. 8063-8071, vol. 81, No. 15.
Evans et al., "Claudin-1 is a Hepatitis C Virus Co-Receptor Required for a Late Step in Entry", Nature, Apr. 12, 2007, pp. 801-805, vol. 446, No. 12.
Flint et al., "Characterization of Infectious Retroviral Pseudotype Particles Bearing Hepatitis C Virus Clycoproteins", Journal of Virology, Jul. 2004, pp. 6875-6882, vol. 78, No. 13.

(Continued)

*Primary Examiner* — Maria Marvich
(74) *Attorney, Agent, or Firm* — Thompson Coburn LLP; Charles P. Romano

(57) ABSTRACT

The human Occludin protein is identified as an essential Hepatitis C Virus (HCV) cell entry factor. Occludin is shown to render murine and other non-human cells infectable with HCV and to be required for HCV-susceptibility of human cells. Associated methods for inhibiting HCV infection, transgenic animal models for HCV pathogenesis, methods of identifying compounds or agents that prevent or mitigate interaction of HCV with Occludin, and HCV inhibitory agents are also disclosed. Kits and cell culture compositions useful for identifying compounds or agents that prevent or mitigate interaction of HCV with Occludin are also provided.

2 Claims, 9 Drawing Sheets

(56) References Cited

OTHER PUBLICATIONS

Hsu et al., "Hepatitis C Virus Glycoproteins Mediate pH-Dependent Cell Entry of Pseudotyped Retroviral Particles", PNAS, Jun. 10, 2003, pp. 7271-7276, vol. 100, No. 12.

Marukian et al., "Cell Culture-Produced Hepatitis C Virus Does Not Infect Peripheral Blood Mononuclear Cells", National Institute of Health—Hepatology, Dec. 2008, pp. 1843-1850, vol. 48, No. 6.

McKeating et al., "Diverse Hepatitis C Virus Glycoproteins Mediate Viral Infection in a CD81-Dependent Manner", Journal of Virology, Aug. 2004, pp. 8496-8505, vol. 78, No. 16.

Scarselli et al., "The Human Scavenger Receiptor Class B Type I is a Novel Candidate Receptor for the Hepatitis C Virus", The EMBO Journal, 2002, pp. 5017-5025, vol. 21, No. 19.

Von Hahn et al., "Hepatitis C Virus Entry", The Journal of Biological Chemistry, Feb. 15, 2008, pp. 3689-3693, vol. 283, No. 7.

Zhang et al., "CD81 is Required for Hepatitis C Virus Glycoprotein-Mediated Viral Infection", Journal of Virology, Feb. 2004, pp. 1448-1455, vol. 78, No. 3.

Keck et al., "Human Monoclonal Antibody to Hepatitis C Virus E1 Glycoprotein That Blocks Virus Attachment and Viral Infectivity", Journal of Virology, Jul. 2004, pp. 7257-7263, vol. 78, No. 13.

Mee et al., "Effect of Cell Polarization on Hepatitis C Virus Entry", Journal of Virology, Jan. 2008, pp. 461-470, vol. 82, No. 1.

"Transgenic mouse services", http://www.ozgene.com/services/transgenics, retrieved from the Internet on Oct 22, 2013, 2 pages.

Ploss et al., "Towards a small animal model for hepatitis C", European Molecular Biology Organization (EMBO) Reports, 2009, pp. 1220-1227, vol. 10, No. 11.

Ryu et al., "Efficient Generation of Transgenic Rats Through the Male Germline Using Lentiviral Transduction and Transplantation of Spermatogonial Stem Cells", Journal of Andrology, Mar./Apr. 2007, pp. 353-360, vol. 28, No. 2.

"Custom Model Generation Publications by Year", http:/www.taconic.com/wmspage.cfm?parm1=3796, retrieved from the Internet on Oct 22, 2013, 11 pages.

Dorner et al., "Study of hepatitis C virus entry in genetically humanized mice", Methods, Feb. 2013, pp. 249-257, vol. 59, No. 2.

Dorner et al., "Completion of the entire hepatitis C virus life cycle in genetically humanized mice", Nature, 2013, pp. 1-7.

* cited by examiner

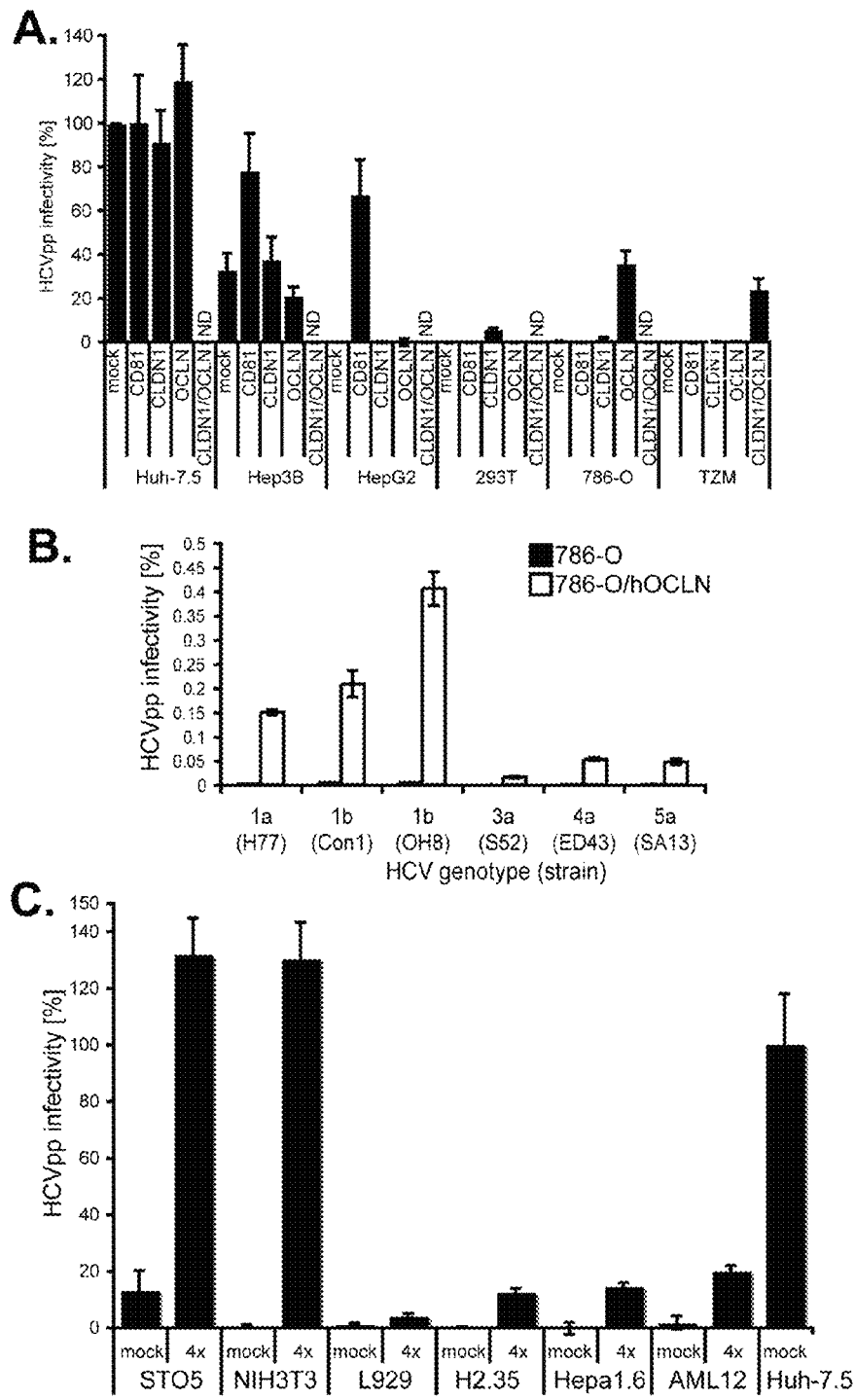
Figure 1 A, B, C

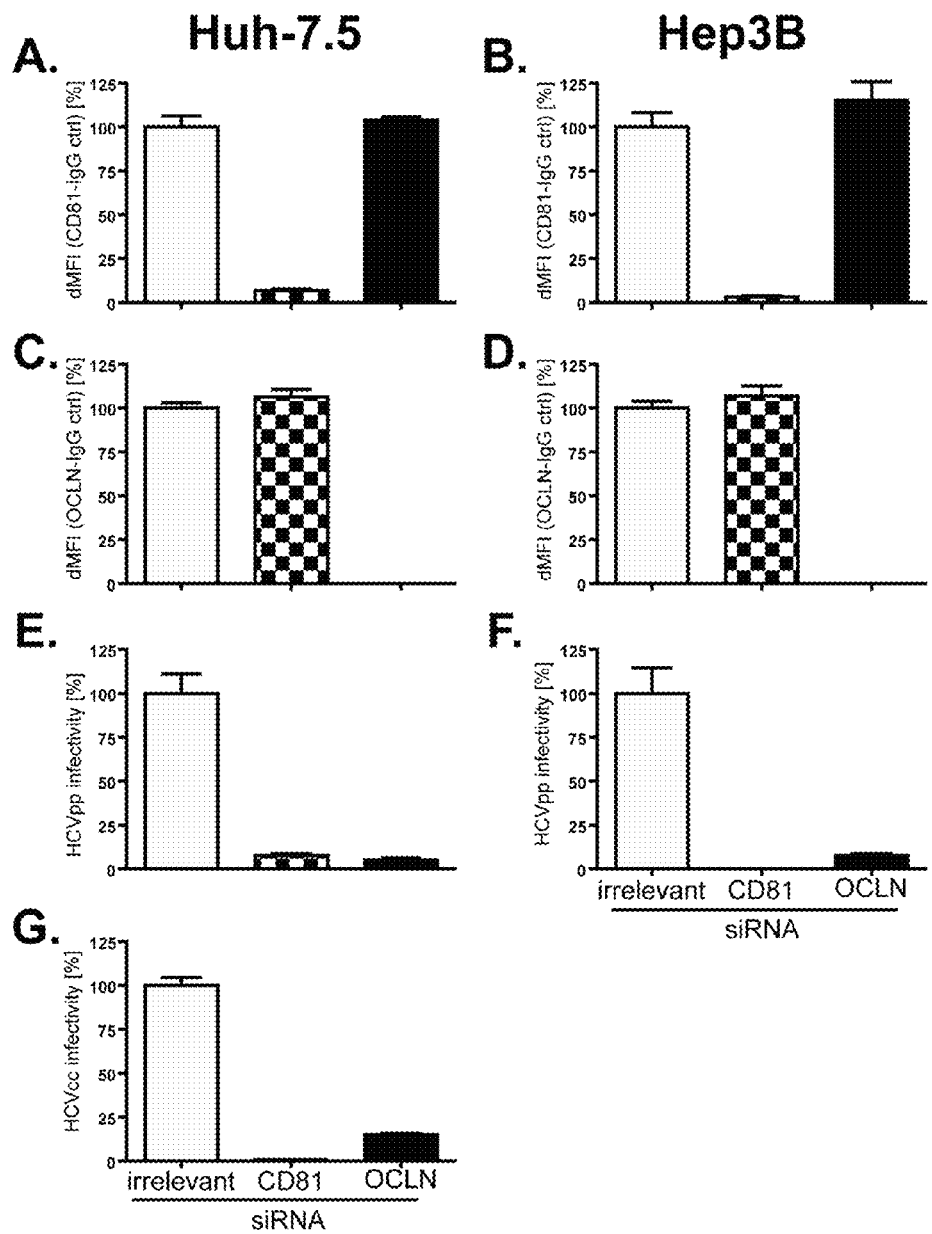
Figure 2 A, B, C, D, E, F, G

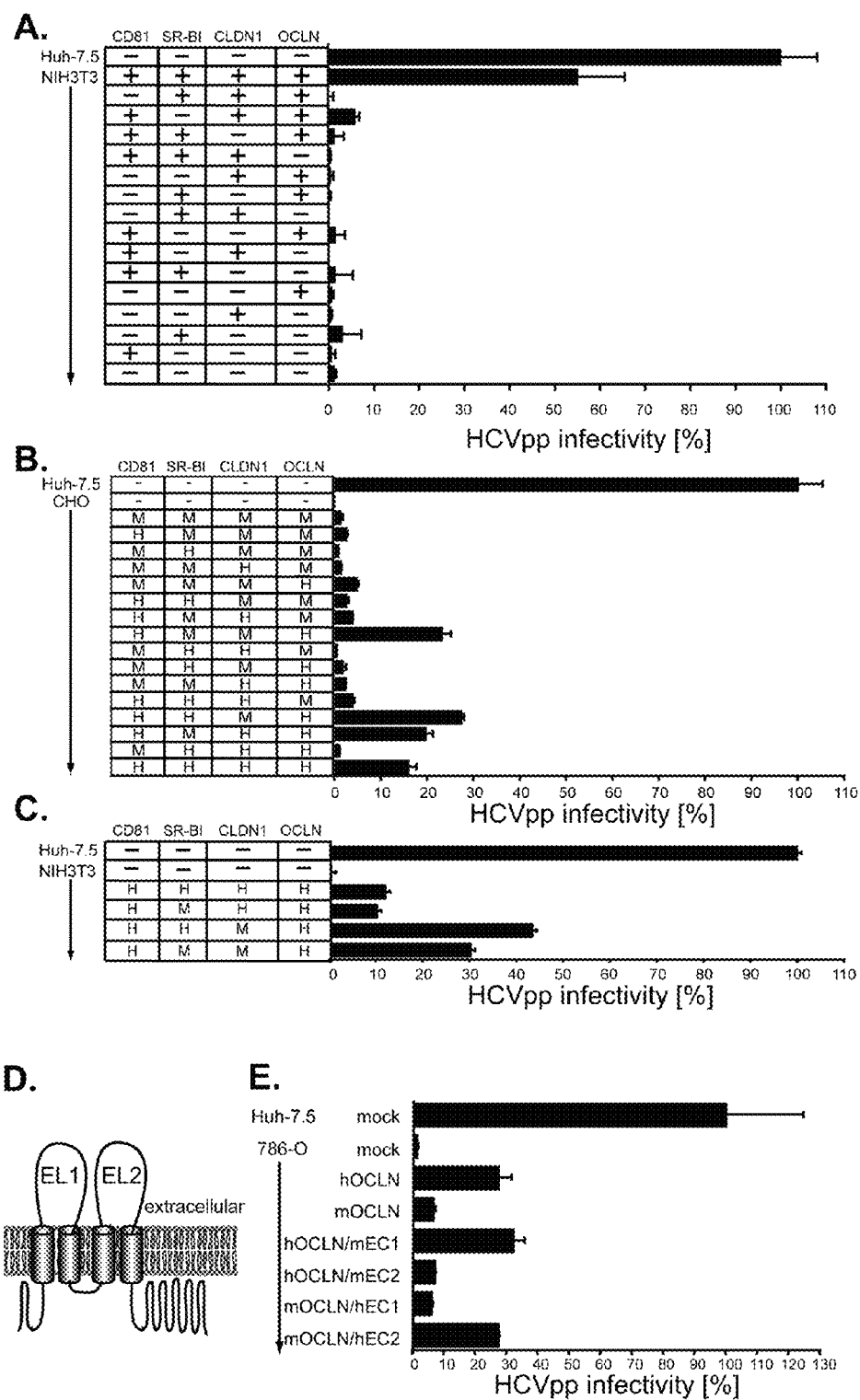
Figure 3 A, B, C, D, E

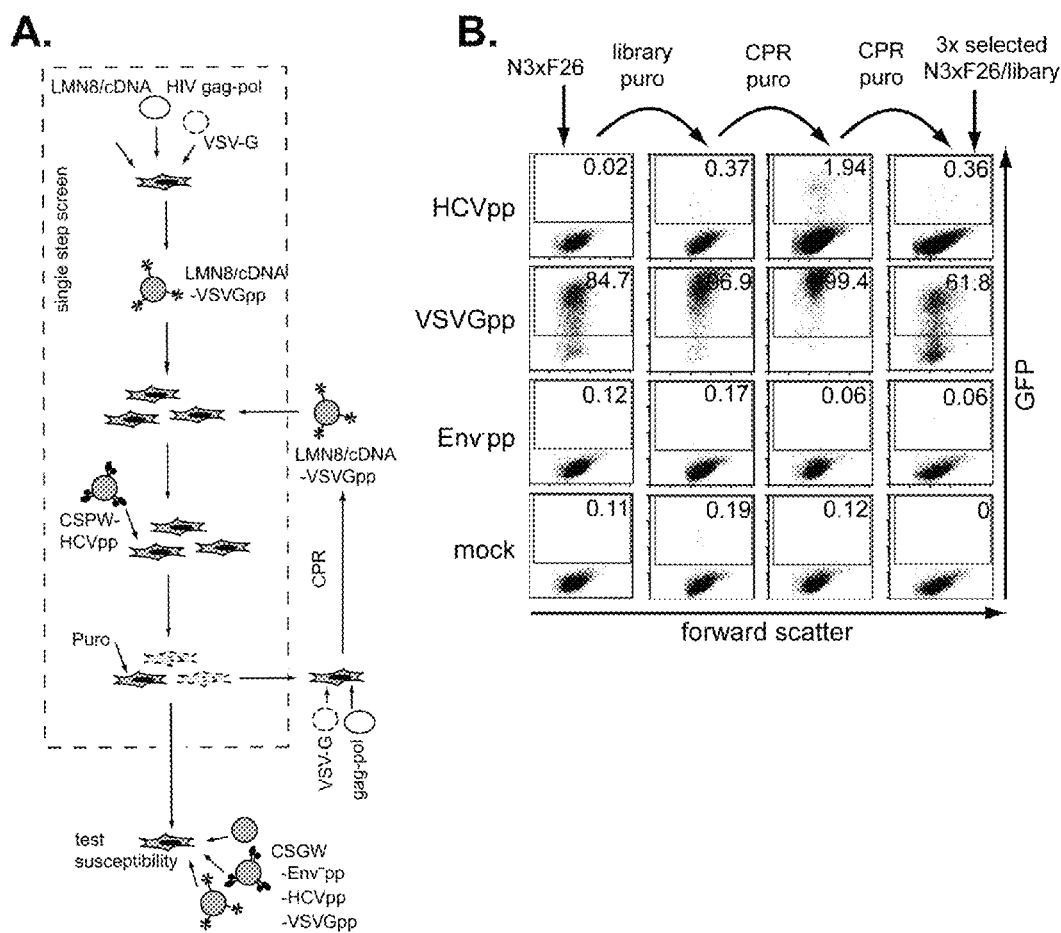
Figure 4 A, B

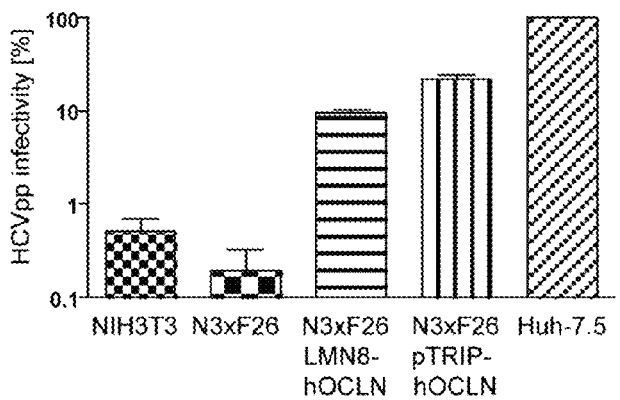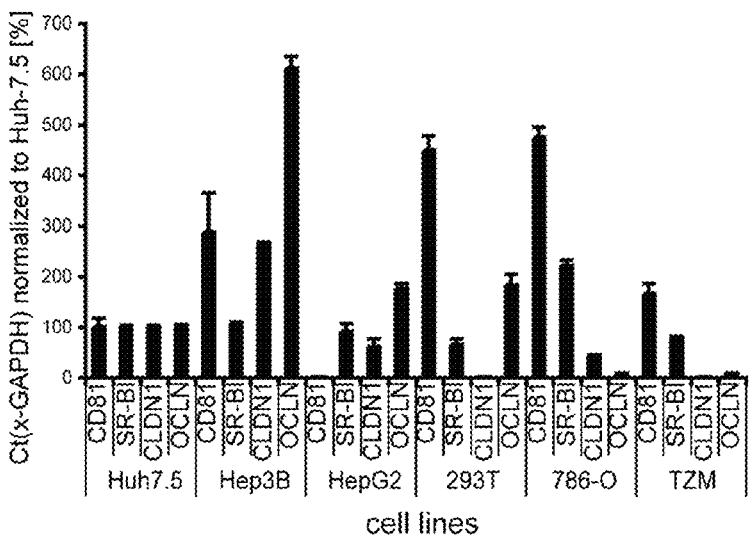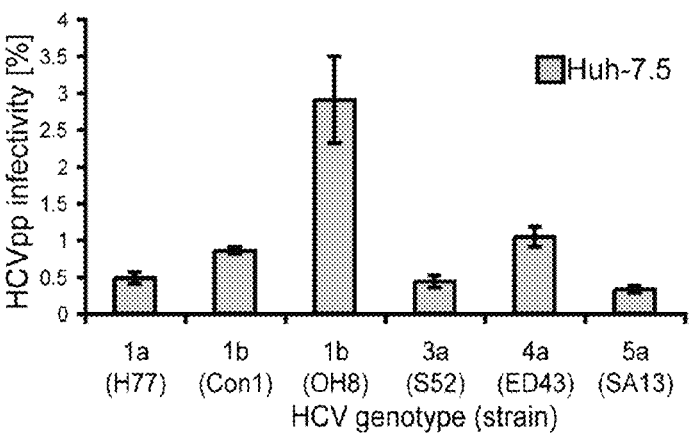
Figure 4 C, D, E

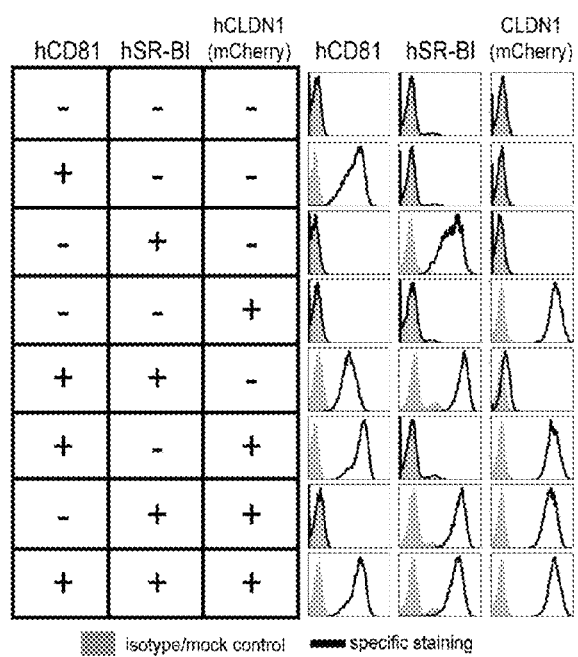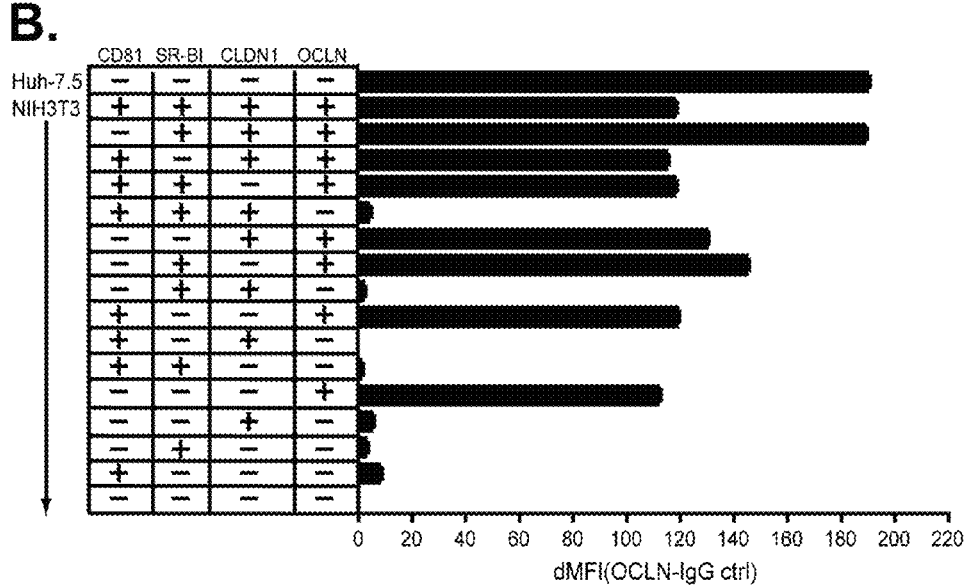
Figure 5 A, B

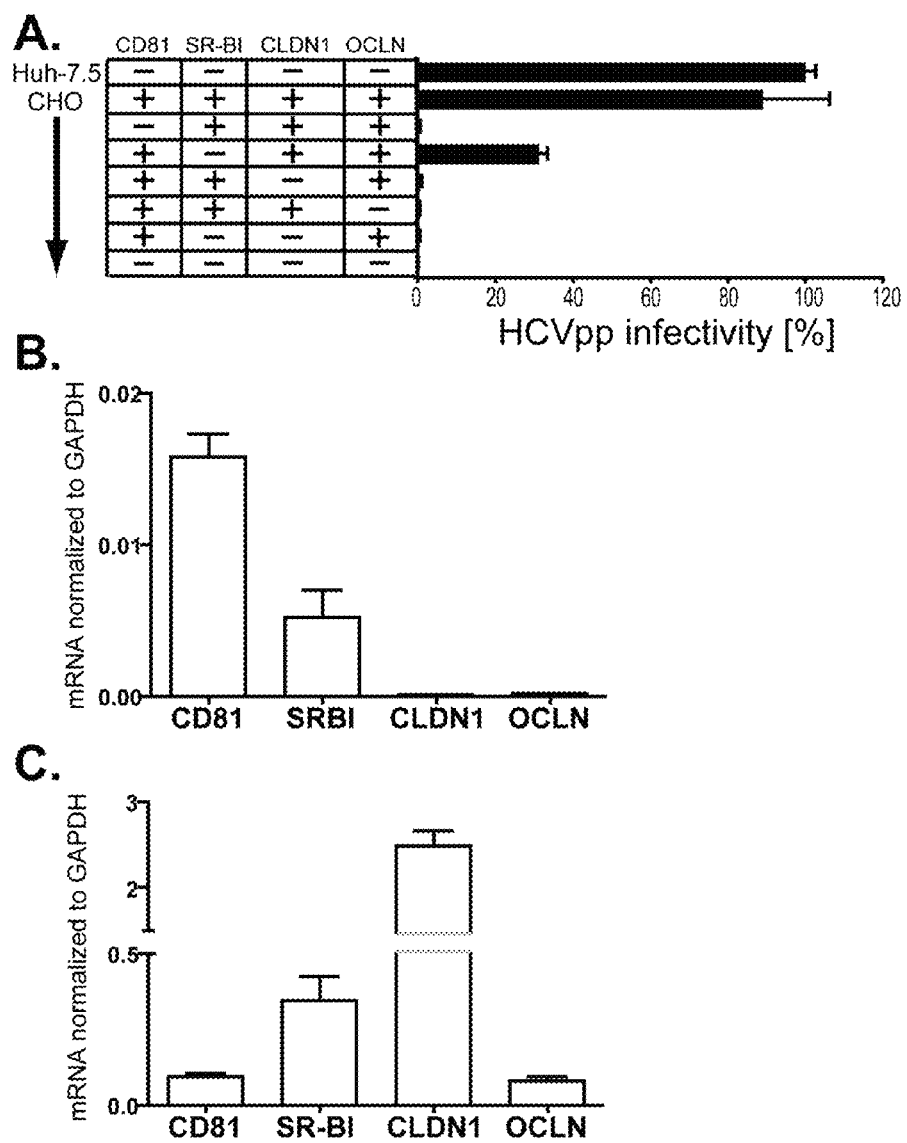
Figure 7 A, B, C

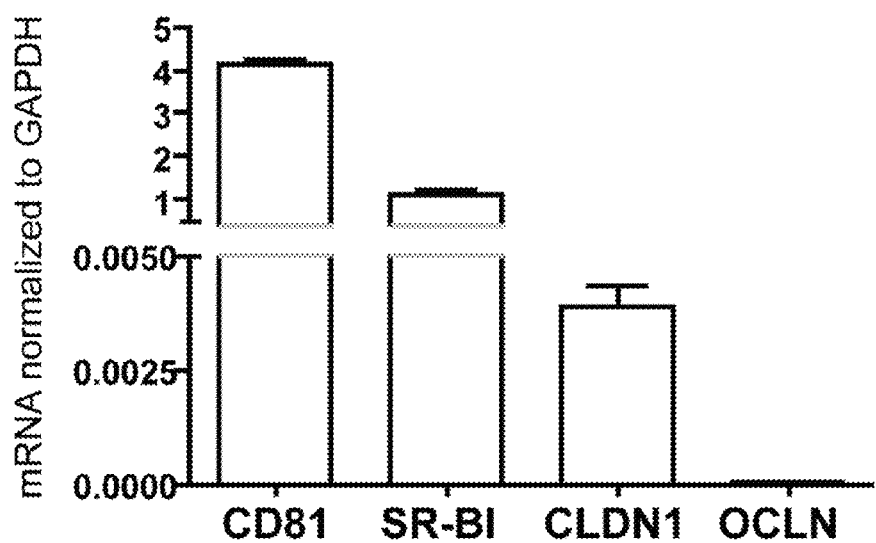
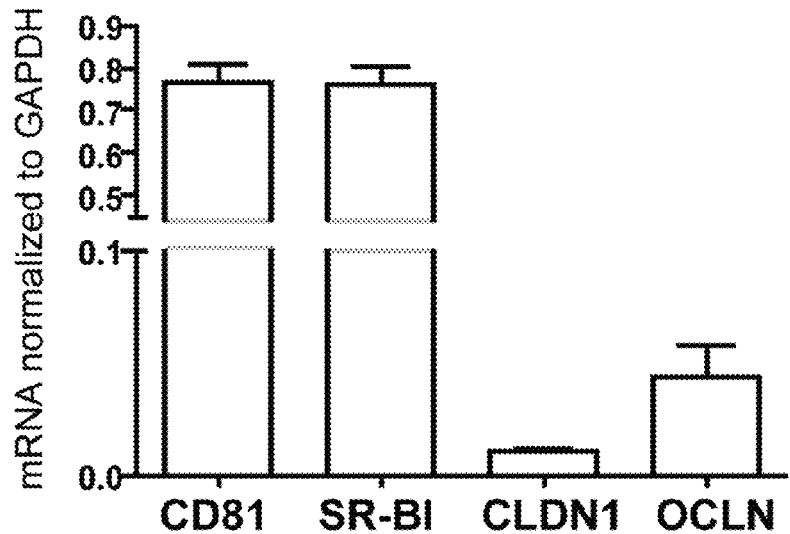
Figure 7 D, E

HCV ENTRY FACTOR, OCCLUDIN

CROSS-REFERENCE TO RELATED APPLICATIONS

This application is a National Stage application of International Patent Application No. PCT/US2009/059285, filed Oct. 1, 2009, which is incorporated herein by reference in its entirety and which claims the benefit of both U.S. Provisional Application Ser. No. 61/102,588, filed Oct. 3, 2008, and U.S. Provisional Application Ser. No. 61/142,262, filed to Jan. 2, 2009, both of which are incorporated by reference herein in their entireties.

GOVERNMENTAL SUPPORT STATEMENT

The subject matter of this application was made with support from the United States Government under the National Institutes of Health (NIH), Grant No. A1072613. The government has certain rights in this invention.

INCORPORATION OF SEQUENCE LISTING

The sequence listing that is contained in the file named "48062_96014_SEQ LST.txt", which is 16788 bytes (measured in operating system MS-Windows), created on Apr. 1, 2011 is filed herewith by electronic submission and incorporated herein by reference in its entirety. The sequence listing contains 48 sequences.

BACKGROUND

Hepatitis C virus (HCV) is a leading cause of liver disease worldwide. The development of much needed specific antiviral therapies and an effective vaccine has been hampered by the lack of a convenient small animal model for this pathogen. The determinants restricting HCV tropism to human and chimpanzee hosts are unknown. Replication of the viral RNA has been demonstrated in mouse cells (25), (29), but these cells are not infectable with either lentiviral particles bearing HCV glycoproteins (HCVpp) (2) or HCV produced in cell culture (HCVcc) (unpublished data), suggesting a block at the level of entry.

U.S. Pat. No. 6,252,045 discloses Occludin sequences, enhanced drug delivery by administration of Occludin inhibitors, and methods of identifying Occludin inhibitors, where an Occludin inhibitor is any substance that enhances paracellular permeability through specific interaction with extracellular protein sequences of Occludin.

SUMMARY OF INVENTION

Through an iterative cDNA library screening approach we have identified human occludin (OCLN) as an essential HCV cell entry factor that is able to render murine cells infectable with HCVpp. Similarly, OCLN is required for HCV-susceptibility of human cells, since its overexpression in uninfectable cells specifically enhanced HCVpp uptake while its silencing in permissive cells impaired both HCVpp and HCVcc infection. In addition to OCLN, HCVpp infection of murine cells required expression of the previously identified HCV entry factors, CD81 (20), scavenger receptor class B type I (SR-BI) (22), and claudin-1 (CLDN1) (11). SR-BI and CLDN1 proteins of human or murine origin function equivalently in HCV entry; both OCLN and CD81, however, must be of human origin to allow efficient infection. The species-specific determinants of OCLN were mapped to its second extracellular loop. The identification of OCLN as a new HCV entry factor further highlights the importance of the tight junction complex in the viral entry process and is a major advance towards developing small animal models for HCV.

HCV virions, lipid-enveloped nucleocapsids bearing the viral glycoproteins E1 and E2, appear to enter a host cell in a highly coordinated process involving components of the virus particle and numerous cellular factors (26). From the long list of putative HCV entry factors, strong evidence supports specific roles for the tetraspanin CD81 (20), SR-BI (22), and the tight junction protein CLDN1 (11). This list appears incomplete, however, as numerous human cell lines and all non-primate cell lines are resistant to HCV entry even when all three human factors are overexpressed (2) (FIG. 4C).

To identify additional factors able to render non-human cells susceptible to HCV entry, we performed a cyclic retrovirus-based repackaging screen of a complementary DNA library derived from the highly HCV-permissive human hepatocarcinoma Huh-7.5 cell line (3). We screened for genes that rendered a non-permissive mouse embryonic fibroblast cell line, NIH3T3, infectable with HCV pseudoparticles (HCVpp), defective lentiviral particles that display the HCV glycoproteins and measure only viral entry (1), (10), (14) (FIG. 4A and Supplementary Methods). To maximize the likelihood identifying a novel component that would permit HCV entry into non-human cells, we utilized an NIH3T3 subclone overexpressing human CD81, SR-BI, and CLDN1. This screen identified human occludin (OCLN) as a potential novel HCV entry factor. OCLN is a four transmembrane domain protein present in the tight junction complex of polarized epithelial cells, where it likely functions to regulate paracellular permeability and cell adhesion (6, 19). Expression of human CD81, SR-BI, CLDN1, and OCLN in NIH3T3 cells enhanced HCVpp infectivity by approximately 120-fold (FIG. 4C).

To confirm that OCLN is required for HCV entry, we examined the relationship between its expression and HCV susceptibility in a variety of human cell lines. Naturally HCV-permissive human hepatocyte cell lines (Huh-7.5 and Hep3B) or those previously shown to lack other entry factors (hepatocellular carcinoma HepG2, and embryonic kidney HEK293T) were found to express readily detectable levels of endogenous OCLN (FIG. 4D). In these cells further overexpression of OCLN did not enhance susceptibility to HCVpp (FIG. 1A). Silencing of OCLN, however, inhibited HCVpp infection of Hep3B cells (FIG. 2F), and both HCVpp and HCVcc infection of Huh-7.5 cells (FIGS. 2, E and G, respectively), indicating that OCLN is essential for HCV infection of naturally permissive cells. This inhibition was HCV-specific, as infection with pseudoparticles bearing the vesicular stomatitis virus glycoprotein (VSVGpp) was not affected (values in FIG. 2, E-F are corrected for VSV-Gpp infectivity). In contrast, the naturally HCV-resistant renal carcinoma cell line, 786-O, expresses high levels of the major HCV entry factors CD81, SR-BI, and CLDN1, but approximately 17-fold less OCLN than Huh-7.5 cells (FIG. 4D). OCLN overexpression in 786-O cells specifically enhanced HCVpp infection by over 88-fold (FIG. 1A). Furthermore, this OCLN-dependence of HCVpp infection was observed across a panel of diverse HCV genotypes (FIG. 1B). Another HCVpp resistant cell line, the HeLa cell-derived cervical carcinoma line TZM, was found to lack both endogenous CLDN1 and OCLN (>100 and 25-fold less mRNA than Huh-7.5 cells, respectively) (FIG. 4D). Overexpression of these factors together increased HCVpp infectivity of TZM cells by 450-fold. These results indicate that OCLN is an essential HCV entry factor.

To further examine HCV entry requirements in non-human cells, we transduced murine NIH3T3 with all combinations of one, two, three, or all four human CD81, SR-BI, CLDN1, and OCLN. Expression levels were determined by expressing an mCherry/CLDN1 fluorescent protein fusion (FIG. 5A) or by FACS staining for CD81, SR-BI (FIG. 5A) and OCLN (FIG. 5B). No combination of human factors enhanced VSVGpp infectivity (data not shown and results in FIG. 3A are normalized to VSVGpp values). Neither human CLDN1 nor SR-BI expression alone dramatically enhanced NIH3T3 HCVpp infection (FIG. 3A). Conversely, populations expressing either human OCLN or CD81 were slightly enhanced (0.5 fold) for HCVpp infection (FIG. 3A), while cells expressing the combination of these two factors were 1.2-fold more infectable with HCVpp (FIG. 3A). The complete set of all four entry factors, however, had a much greater impact on HCVpp permissivity, with a 45-fold increase over naïve NIH3T3 cells (FIG. 3A). Furthermore, expression of all four factors conferred HCV-susceptibility to mouse embryonic fibroblast cell lines, STO5 and L929, as well as the mouse hepatocyte cell lines, AML12, Hepa1.6, and H2.35, with enhancements of 4 to 85-fold over naïve cells (FIG. 1C). Permissivity to VSVGpp was not affected by expression of the human proteins. Attempts to infect these murine cells with HCVcc were unsuccessful, likely as a result of inefficient viral RNA replication in these cells, as previously documented (24) (29).

To investigate which of the four entry factors are responsible for HCV species-specific tropism, we transduced Chinese hamster ovary (CHO) cells with every combination of human and mouse CD81, SR-BI, CLDN1 and OCLN. Expression of all four human factors specifically enhanced HCVpp infection of CHO cells by 336-fold (FIG. 3B). Conversely, expression of the four mouse proteins enhanced HCVpp infectivity by only 18-fold (FIG. 3B). In all combinations, mouse SR-BI and CLDN1 functioned equivalently to that of human origin (FIG. 3B). This agrees with our previous observation that in human cells both human and mouse CLDN1 proteins, which are 90% identical, are equally functional as HCV entry factors (11), and shows for the first time that mouse and human SR-BI are equally capable of mediating HCV uptake. It is noteworthy that none of the mouse cells examined above express high levels of either murine SR-BI or CLDN1, thus explaining their dependence on transduction of these proteins for HCVpp permissivity. In contrast, CD81 and OCLN exhibited species-specific HCV entry factor functionality in CHO and NIH3T3 cells. CHO cells expressing either of these human proteins in the context of the other three mouse proteins were slightly more permissive to HCVpp than cells expressing only the mouse proteins (FIG. 3B). Furthermore, expression of both human CD81 and OCLN, together with murine SR-BI and CLDN1, rendered CHO cells as infectable with HCVpp as cells expressing all four human factors (FIG. 3B, compare last bar to any with human CD81 and OCLN). These results agree with our previous finding that mouse and hamster CD81, when expressed in the CD81-deficient human hepatocellular carcinoma cell line HepG2, support only low level HCV entry (greater than 10-fold reduced from human CD81) (13). Importantly, these data indicate that CD81 and OCLN represent the minimal human-specific entry factors, at least in the context of mouse and hamster cells.

For CD81, the species-specific difference in HCV-entry activity between rat and human proteins maps exclusively to its large extracellular loop (13). To determine the regions of OCLN that are responsible for the functional difference observed between mouse and human proteins, which are 91% identical, we expressed chimaeric OCLN molecules in 786-O cells and assayed HCVpp permissivity. In these experiments, a mouse chimaera bearing the second extracellular loop (EC2) of human OCLN was as active as the full-length human protein and at least 4-fold more active than the mouse homologue (FIG. 3D, compare mOCLN/hEC2 to hOCLN and mOCLN, respectively). Conversely, a human OCLN mutant with the EC2 of the mouse protein functioned similarly to the full-length mouse factor in HCVpp infectivity (FIG. 3D, compare hOCLN/mEC2 to mOCLN). These data suggest that the human-specific determinants of OCLN HCV entry factor functions are entirely contained within EC2.

This study represents a major step forward in understanding both HCV host cell entry and HCV species tropism. All human, murine, or hamster cell lines that we tested became permissive for HCV entry when engineered to express the molecules CD81, SR-BI, CLDN1, and OCLN. This suggests that OCLN completes the list of cell-type specific HCV entry factors; any other factors required for HCV entry must be ubiquitously expressed. The fact the OCLN is a major component of the tight junction complex further highlights the significance of this structure and cell polarity to HCV entry. We previously showed that CLDN1 acts late in the entry process, just prior to virion internalization (11). The intimate association of CLDN1 and OCLN at the tight junction suggests that both these factors may function in a similar time frame. The use of multiple uptake factors with distinct cell surface distributions strengthens the hypothesis that HCV follows a coordinated entry pathway similar to that of coxsackievirus B. This virus initially interacts with a primary receptor (decay-accelerating factor) on the luminal cell surface, followed by lateral migration of the virus-receptor complex to the tight junction, where interaction with the Coxsackie Adenovirus receptor co-receptor is immediately followed by uptake into the host cell (7). Strikingly, coxsackievirus B entry also requires OCLN (8), further suggesting similar entry mechanisms of this virus and HCV. Recent work by Brazzoli et al. supports this step-wise model of HCV entry, demonstrating that initial engagement of CD81 on the cell surface, by either fluorescently labeled CD81 antibodies or soluble forms of the HCV glycoproteins, is followed by GTPase-dependant actin rearrangements that allow lateral movement of the CD81-bound complex into areas of cell-cell contact overlapping with both CLDN1 and OCLN localization (4).

The study of HCV pathogenesis and the development of urgently needed effective antivirals and therapeutic and/or preventative vaccines targeting this virus has been severely hampered by the lack of convenient inbred small animal models capable of supporting HCV infection and replication. Numerous blocks will certainly need to be overcome before complete viral replication in a mouse can be achieved. HCV RNA replication in mouse cells is inefficient (25), (29), and the ability of such cells to support virion assembly is unknown. Our results clearly demonstrate, however, why mouse cells are unable to support HCV entry. This major block to HCV replication in murine cells can now be overcome simply by the expression of human CD81 and OCLN in the context of mouse CLDN1 and SR-BI, providing a clear platform upon which a mouse model for HCV infection can be constructed.

Methods of inhibiting, mitigating or preventing infection of a subject with Hepatitis C Virus (HCV) that can comprise contacting a cell in said subject with an agent which inhibits HCV interaction with an Occludin protein, wherein said interaction includes any direct or indirect function of Occludin required for HCV entry are embodiments of the methods, the subject is a mouse, a rat, a monkey, or a human. In certain embodiments of the methods, the agent binds to an extracellular loop of the Occludin protein. In certain embodiments, the agent is selected from the group consisting of an antibody, an aptamer, or a recombinant protein. In certain embodiments where the agent is an antibody, the antibody can be a monoclonal or a single chain antibody.

Also provided herein are transgenic animal models for the study of Hepatitis C Virus (HCV) pathogenesis, where the models comprise expression of a human Occludin transgene in said animal, whereby expression of said human Occludin transgene renders the animal permissive for Hepatitis C Virus (HCV) infection. In certain embodiments, the transgenic animal model is one wherein the animal is selected from the group consisting of a mouse, a monkey, and a rat.

Also provided are methods for screening for an inhibitor of Hepatitis C Virus (HCV) infection, where the methods comprise screening a library for a compound which prevents or mitigates binding of a region of a Hepatitis C Virus with a region of an Occludin protein.

Also provided are methods of identifying a compound or agent that prevents or mitigates interaction of a region of a Hepatitis C Virus with a region of a Occludin protein, where the methods comprise the steps of: a) providing either i) a recombinant protein comprising at least an extracellular loop of Occludin protein or conservative amino acid substitutions thereof, or ii) a cell comprising a recombinant vector that provides for expression of a membrane bound protein comprising an extracellular loop of a Occludin protein, wherein said amino acid residues of said Occludin protein are located extracellularly to said cell; b) contacting said protein or said cell from step (a) with an agent or a compound and an HCV envelope protein, a cell expressing HCV envelope proteins EI and E2, an HCV pseudotyped retroviral particle, an HCV cell culture particle, an ex vivo HCV cell culture particle or HCV; and c) determining if said compound or agent inhibits interaction or fusion of said protein or said cell provided in (a) with said HCV envelope protein, said cell expressing HCV envelope proteins EI and E2, said HCV pseudotyped retroviral particle, said HCV cell culture particle, said ex vivo HCV cell culture particle, or said HCV provided in step (b), thereby identifying a compound or agent that prevents or mitigates interaction of a region of a Hepatitis C Virus with a region of an Occludin protein. In certain embodiments of the methods, the cell in step (a) is a CD81 positive cell, SR-BI positive cell, and/or a Claudin-1 positive cell. In certain embodiments of the methods, the cell in step (a) is a NIH3T3, L929, H2.35, Hepa1.6, AML12, CHO, 786-O, or TZM cell. In certain embodiments of the methods, the recombinant vector is a DNA vector or an RNA vector. In certain embodiments of the methods, the agent in step (b) is provided by an antibody library, an aptamer library, a peptide library, a recombinant protein library or a peptidomimetic library. In certain embodiments of the methods, inhibition of interaction of said recombinant protein of step (a) is determined in step (c) by assaying for retention of the recombinant protein by said HCV envelope protein, by said cell expressing HCV envelope proteins EI and E2, said HCV pseudotyped retroviral particle, by said HCV cell culture particle, said by ex vivo HCV cell culture particle, or by said HCV provided in step (b), wherein decreased retention of the recombinant protein is indicative of binding inhibition. In certain embodiments of the methods, determination of interaction or fusion in step (c) is effected by assaying a reporter protein. In certain embodiments, the methods of identifying a compound or agent that prevents or mitigates interaction of a region of a Hepatitis C Virus with a region of a Occludin protein can further comprise any one of, or both of, the step(s) of: i) screening for an agent or compound that does not enhance paracellular permeability through specific interaction with an extracellular protein sequence of Occludin; and/or ii) screening for an agent or compound that does not inhibit Occludin-dependent cell adhesion. Techniques for: i) screening for an agent or compound that does not enhance paracellular permeability through specific interaction with an extracellular protein sequence of Occludin; and for ii) screening for an agent or compound that does not inhibit Occludin-dependent cell adhesion include, but are not limited to, those disclosed in U.S. Pat. No. 6,252,045, which is incorporated herein by reference in it's entirety.

Also provided are agents that prevent or mitigate interaction of a region of a Hepatitis C Virus with an extracellular loop of an Occludin protein, wherein said agent is an antibody, an aptamer, a peptide, a peptidomimetic compound, or a recombinant protein, and wherein said interaction includes any direct or indirect function of Occludin required for HCV entry. In certain embodiments, the agent does not enhance paracellular permeability through specific interaction with an extracellular protein sequence of Occludin. In certain embodiments, the agent does not inhibit Occludin-dependent cell adhesion. In still other embodiments, the agent does not does not enhance paracellular permeability through specific interaction with an extracellular protein sequence of Occludin and does not inhibit Occludin-dependent cell adhesion.

Also provided are kits for identifying a compound or agent that prevents or mitigates interaction of a region of a Hepatitis C Virus with a region of a Occludin protein, said kit comprising either i) a recombinant protein comprising an extracellular loop of an Occludin protein or conservative amino acid substitutions thereof, or ii) a recombinant vector that provides for expression of a membrane bound protein comprising an extracellular loop of an Occludin protein or conservative amino acid substitutions thereof, wherein said amino acid residues of said Occludin protein are located extracellularly to a cell expressing said membrane bound protein, or iii) a cell comprising said recombinant vector; and instructions for using said kit to identify a compound or agent that prevents or mitigates interaction of a region of a Hepatitis C Virus with a region of a Occludin protein. In certain embodiments, the kit further comprises an HCV envelope protein, a recombinant vector encoding HCV envelope proteins EI and E2, a recombinant vector encoding an HCV pseudotyped retroviral particle, a recombinant vector encoding an HCV cell culture particle, or a recombinant vector encoding an infectious HCV particle.

Also provided are cell culture compositions comprising: i) a cell comprising a recombinant vector that provides for expression of a membrane bound protein comprising an Occludin Protein or conservative amino acid substitutions thereof, wherein said amino acid residues of said Occludin protein are located extracellularly to said cell, and either ii) a cell comprising a recombinant vector that encodes HCV envelope proteins EI and E2 or iii) any one of a HCV pseudo typed retroviral particle, a HCV cell culture particle, an ex vivo HCV cell culture particle, or an HCV particle. In certain embodiments of such cell culture compositions, the HCV pseudotyped retroviral vector comprises an HCV EI protein, an HCV E2 protein and a packaging competent retroviral genome containing a reporter gene. In certain embodiments of such cell culture compositions, the packaging competent retroviral genome is an HIV or an MLV packaging competent retroviral genome. In certain embodiments of such cell culture compositions, the packaging competent retroviral genome is an envelope deficient retroviral genome.

BRIEF DESCRIPTION OF THE DRAWINGS

FIG. 1. OCLN expression confers susceptibility to HCVpp. A, The indicated human cell lines were either mock transduced or transduced to express human pTRIP-mCherry-CD81 (CD81), pTRIP-Cerulean-CLDN1 (CLDN1), pTRIP-Venus-OCLN (OCLN), or both CLDN1 and OCLN. Parallel cultures of these populations were then separately challenged with HCVpp and VSVGpp encoding GFP reporters. HCVpp infectivity is reported as the titer of HCVpp divided by the titer of VSVGpp, after subtraction of the signals from infection with non-enveloped pseudoparticles (Env-pp), as described in the materials and methods. B, GFP-encoding pseudoparticles bearing the indicated glycoproteins from different HCV genotypes (isolate name in parentheses) were used to infect naive (black) or OCLN-expressing (white) 786-O cells. C, The indicated mouse cells lines were either mock transduced or transduced to express a combination of human pTRIP-mCherry-CD81 (CD81), pTRIP-SR-BI (SR-BI), pTRIP-Cerulean-CLDN1 (CLDN1) and pTRIP-Venus-OCLN (OCLN) (4x). Parallel cultures, as well as permissive Huh-7.5 cells, were then challenged with HCVpp and VSVGpp encoding GFP reporters and HCVpp infectivity calculated as above. Means and standard deviation (SD) of at least triplicate experiments are shown.

FIG. 2. OCLN silencing inhibits HCV entry. Huh-7.5 (left column) and Hep3B (right column) were transfected with irrelevant (gray bars), CD81 (checkered bars), or OCLN (black bars) specific siRNA pools. To determine expression levels, each cell population was stained with CD81 (A and B) and OCLN (C and D) specific antibodies. Protein expression was analyzed by flow cytometry; the ratio between specific and isotype control staining is shown. At the time of expression analysis, parallel siRNA-treated cells were challenged with HCVpp (E and F) and HCVcc (G). HCVpp infectivity was calculated and normalized as described in the materials and methods. HCVcc infection was quantified by the ratio of viral protein (NS5A) staining to isotype control staining. All samples are normalized to irrelevant siRNA treated cells. dMFI, the difference in the mean fluorescence intensity. Means and SD of at least triplicate experiments are shown.

FIG. 3. Expression of human OCLN and human CD81 determines HCV species tropism. (A) Mouse NIH3T3 were transduced with combinations of human pTRIP-CD81 (CD81), pTRIP-SR-BI (SR-BI), pTRIP-mCherry-CLDN1 (CLDN1) and pTRIP-OCLN (OCLN). Hamster CHO (B) and NIH3T3 (C) cells were transduced with combinations of human (H) and mouse (M) pTRIP-mCherry-CD81 (CD81), pTRIP-SR-BI (SR-BI), pTRIP-Cerulean-CLDN1 (CLDN1) and pTRIP-Venus-OCLN (OCLN). D, Diagram of OCLN membrane topology (12). E, 786-O cells were transduced with mouse/human OCLN chimaeras; all chimaeras were N-terminally tagged with Venus yellow fluorescent protein. Transduced cells (A, B, C and E) were challenged with HCVpp and VSVGpp encoding GFP reporters and HCVpp infectivity calculated and normalized as described in methods. Means and SD of at least duplicate experiments are shown.

FIG. 4. Identification of OCLN as an HCV entry factor. A, Illustration of the screen for cDNAs conferring HCVpp-susceptibility to NIH3T3 cells expressing human CD81, SR-BI and mCherry/CLDN1 (N3xF26). The initial Huh-7.5-derived library, in a LMN8 murine leukemia virus (MLV)-based retroviral vector, was packaged into VSVGpp by co-transfection of 293T cells with the library DNA and vectors expressing MLV gag-pol and VSV-G. Naïve N3xF26 cells were then transduced with the pseudoparticle library and challenged with HCVpp encoding a puromycin resistance gene (CSPW) followed by antibiotic selection. Surviving clones were pooled, expanded, and tested for susceptibility to pseudoparticles bearing no glycoprotein (Env-pp), HCVpp and VSVGpp encoding a GFP reporter (CSGW). The population was subsequently transfected with MLV gag-pol and VSV-G to produce VSVGpp encoding the LMN8 genomes with the cDNA inserts contained in the surviving N3xF26 cells (cyclic packaging rescue, CPR). These re-packaged pseudoparticles were used to transduce naïve N3xF26 cells for subsequent rounds of screening. CSPW proviruses are HIV-1 based and thus not repackaged during the MLV gag-pol mediated CPR step. In addition, this provirus contains a deletion in the 3'LTR that prevents expression of packagable viral RNA in transduced cells. B, HCVpp permissivity of N3xF26 cells increased during multiple rounds of library transduction and selection. Naïve N3xF26 cells (first column) or aliquots of N3xF26 cells transduced with the parental ($2^{nd}$ column) or repackaged ($3^{rd}$ and $4^{th}$ column) LMN8-cDNA library were assessed for permissivity to Env-pp, HCVpp, or VSVGpp encoding a GFP reporter (CSGW). GFP expression was measured by flow cytometry 72 h after infection. Actions performed between assays are denoted on the top: library—initial transduction of the cDNA library; puro—transduction with HCVpp encoding a puromycin resistance reporter gene followed by puromycin selection; CPR—transfection of MLV gag-pol and VSV-G to repackage the cDNAs contained in the N3xF26 cell population into pseudoparticles for delivery to naïve N3xF26 cells and further selection. The percentage of GFP positive cells is indicated in the upper right corner of each plot. After two rounds of selection including one repackaging steps the effective HCVpp titer on the selected population increased by about 100-fold ($3^{rd}$ column). After three rounds of selection including two repackaging steps the effective HCVpp titer increased about 20-fold compared to naïve N3xF26 cells (top row) whereas the effective titers of VSV-Gpp ($2^{nd}$ row) and Env-pp ($3^{rd}$ row) were essentially unchanged or even decreased. Of 24 cell clones isolated by FACS after 3 rounds of selection, eight harbored a cDNA encoding OCLN. No cDNA could was found in the remaining 16 clones, likely representing untransduced cells selected through nonspecific uptake of HCVpp. All of the LMN8-OCLN cDNA clones contained an identical amino-terminally truncated OCLN cDNA fragment that expressed an OCLN protein missing the first 140 amino acids, essentially removing the intracellular N-terminal tail. C, LMN8-VSVGpp encoding the isolated N-terminally truncated OCLN as well as pTRIP-VSVGpp encoding the full-length OCLN were used to transduce naïve N3xF26 cells. These cells were then challenged with GFP encoding pseudoparticles. HCVpp infectivity is reported as the titer of HCVpp divided by the titer of VSVGpp, after subtraction of Env-pp signals, as described in the materials and methods. Values are normalized to parallel infections of highly permissive Huh-7.5 cells. D, Total RNA was isolated from the indicated cell lines and the human CD81, CLDN1 and OCLN mRNA levels were determined by RT-quantitative PCR. Data were normalized to GAPDH expression and plotted as percentage of Huh-7.5 cells. Means and standard deviations (SD) of at least triplicate experiments are shown. E, HCVpp percent infectivity in Huh-7.5 for various HCVpp of HCV genotypes (and strains) 1a(H77), 1b (Con1), 1b(OH8), 3a(S52), 4a(ED43), and 5a(SA13) are shown.

FIG. 5. Expression of HCV entry factors in transduced cells. Mouse NIH3T3 were transduced in the indicated combinations with human pTRIP-CD81 (CD81), pTRIP-SR-BI (SR-BI), pTRIP-mCherry/CLDN1 (CLDN1) and pTRIP-OCLN (OCLN). CD81, SR-BI and CLDN1 (A) and OCLN expression (B) were monitored by flow cytometry at the time of infection. dMFI, the difference in the mean fluorescence intensity. Means and SD of at least triplicate experiments are shown.

FIG. 7. CD81, SR-BI, CLDN1 and OCLN constitute the minimal set for efficient HCVpp entry into nonhuman cells. A, Hamster CHO cells were transduced with the indicated combinations of human pTRIP-mCherry-CD81 (CD81), pTRIP-SR-BI (SR-BI), pTRIP-Cerulean-CLDN1 (CLDN1) and pTRIP-Venus-OCLN (OCLN). Transduced cells were challenged with HCVpp and VSVGpp encoding GFP reporters and HCVpp infectivity calculated and normalized as described in the materials and methods. Total RNA was isolated from CHO (B) and NIH3T3 (D), hamster (C) and mouse (E) liver and the hamster or mouse CD81, CLDN1 and OCLN mRNA levels were determined by RT-quantitative PCR. Data were normalized to GAPDH expression. Means and SD of at least duplicate experiments are shown.

DETAILED DESCRIPTION

Figure 6:
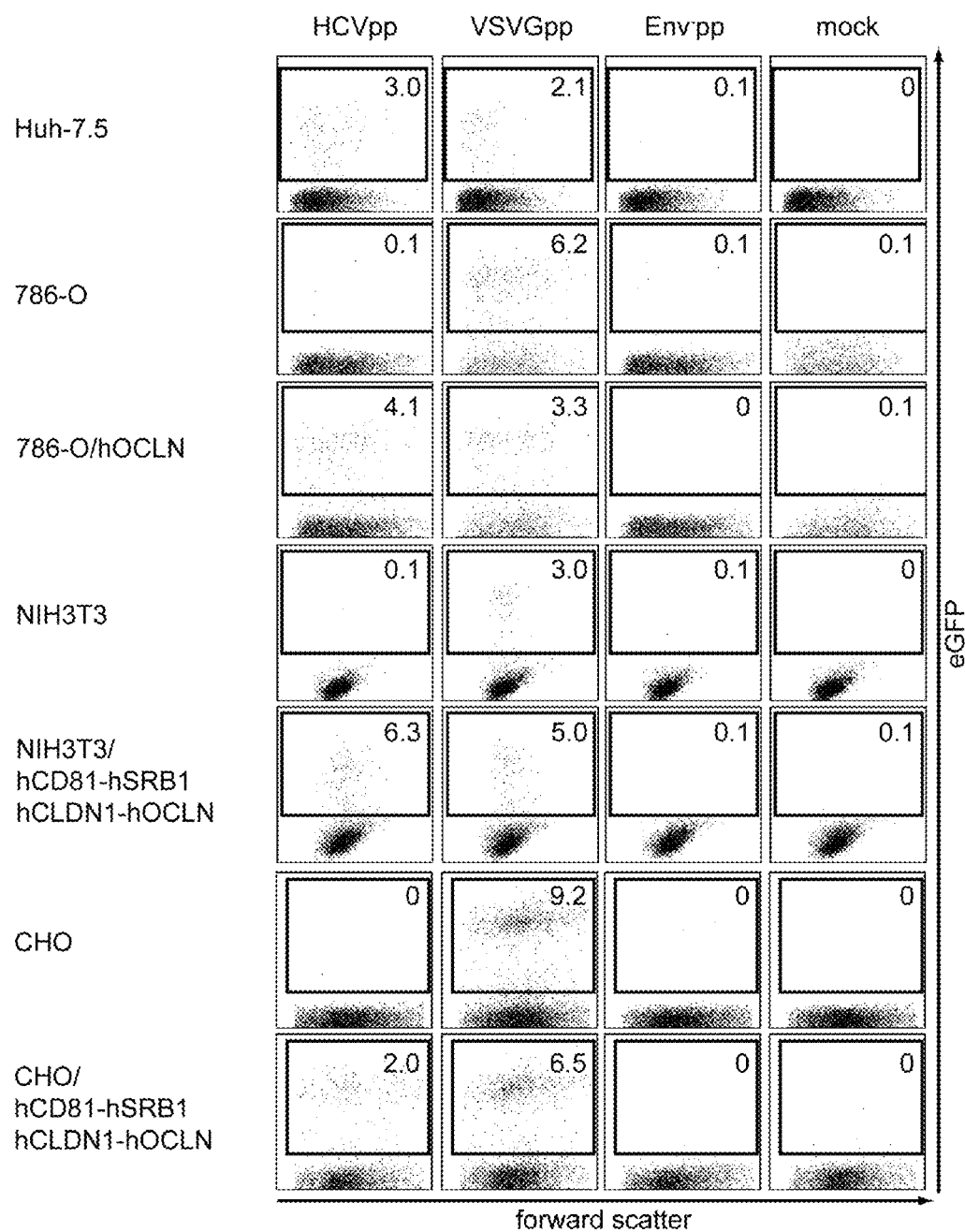
FIG. 6. Selected raw data of HCV entry in human, mouse and hamster cells as analyzed by flow cytometry. Human (Huh7.5, 786-0), mouse (NIH3T3) and hamster (CHO) cells were transduced as indicated with human pTRIP-mCherry-hCD81 (hCD81), pTRIP-Cerulean-hCLDN1 (hCLDN1), pTRIP-Venus-hOCLN (hOCLN) and then challenged in parallel with HCVpp, VSVGpp or Env-pp. Shown are FACS plots representative of those that have been used for the calculations of HCV infectivity in all other analyses.

The following disclosed embodiments are merely representative of the invention, which may be embodied in various forms. Thus, specific structural and functional details disclosed herein are not to be interpreted as limiting.

All reagents and chemicals are either commercially available or can be prepared by standard procedures found in the literature or are known to those of skill in the arts of cell or molecular biology, organic chemistry, biochemistry, and the like.

DEFINITIONS

As used herein, the term "HCV" refers to any major HCV genotype, subtype, isolate, and/or quasispecies. HCV genotypes include, but are not limited to, genotypes 1, 2, 3, 4, 5 and 6 and HCV subtypes include, but are not limited to, subtypes Ia, Ib, 2a, $2b_5$ 2c, 3a, 4a-4f, 5 a, and 6a.

As used herein, the phrase "conservative amino acid substitutions" refers to one or more changes in amino acid(s) in a sequence is (are) are replaced with another amino acid(s), the charge and polarity of which is similar to that of the native amino acid. Conservative substitutes for an amino acid within a protein, a peptide, or peptidomimetic compound are made with members of the group to which the originally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; (4) neutral nonpolar (hydrophobic) amino acids such as alanine, leucine, isoleucine, valine, proline, phenylalanine, tryptophan, and methionine. Conservative amino acid changes can be made by substituting one amino acid within one of these groups with another amino acid within the same group.

As used herein, an "antibody" is any of a polyclonal antibody, a monoclonal antibody, a single chain antibody, or a synthetic antibody.

As used herein, a "monoclonal antibody" is any antibody derived from any source that recognizes a single epitope.

As used herein, a "single chain antibody" is any light chain antibody, any heavy chain antibody, or any fragment thereof comprising an antigen recognition site. Single chain antibodies can be derived from any source.

As used herein, a "synthetic antibody" is any antibody that is produced by recombinant DNA technology. Synthetic antibodies thus include, but are not limited to, humanized antibodies, mutagenized antibodies, and antibodies derived from human, bacterial, yeast or bacteriophage expression libraries.

As used herein, the phrase "peptidomimetic compound" refers a peptide analog containing one or more non-naturally occurring amino acids (e.g., non-natural side chains, non-natural chiralities, N-substituted amino acids, or beta amino acids), non-natural topologies (e.g., cyclic or branched) and/or peptide analogues with partially or totally substituted amide (peptide) bonds with ester, thioester or other linkages.

As used herein, the phrase "chemically derivatized variant", when used in reference to a peptide or peptidomimetic compound, refers to peptides or peptidomimetic compounds that have been covalently modified. Covalent modifications include, but are not limited to, acetylation, amidation, sulfation, succinylation, methylation, chelator linkage or terminal blockage.

As used herein, the term "corresponding", when used in the context of comparing, aligning, or identifying equivalent amino acids in one polypeptide sequence with another polypeptide, peptide, or peptidomimetic compound sequence, refers to the comparison or alignment that will yield the highest percent identity when aligned with the other polypeptide sequence.

As used herein, the phrase "membrane bound protein" refers to any protein that is bound to a cell membrane under physiological pH and salt concentrations. Binding of the membrane bound protein can be either by direct binding to the phospholipid bilayer or by binding to a protein, glycoprotein, or other intermediary that is bound to the membrane.

As used herein, the term "extracellular" refers to the external, non-cytoplasmic region of a cell.

As used herein, the phrase "interaction of a region of a Hepatitis C Virus with a region of an Occludin protein", encompasses any step in the process by which an HCV virion or component derived there from is recognized, bound and/or internalized by a cell. As used herein, interactions include any direct or indirect function of Occludin required for HCV entry.

Methods of Inhibiting, Mitigating or Preventing HCV Infection by Inhibiting HCV Interaction with an Occludin Protein.

A variety of methods for inhibiting HCV infection by inhibiting endogenous Occludin function are contemplated by this invention. Such methods can comprise either blockage of regions of endogenous Occludin that provide for cellular interactions required for HCV entry or blockage of the regions of HCV that provide for interactions with endogenous Occludin or an Occludin containing protein complex. Similar methods for inhibiting HCV infection by inhibiting endogenous Claudin function are also described in WO 2007/130646.

Having identified the region of an endogenous Occludin that can be bound to inhibit HCV infection, a variety of effective extracellular loop binding agents are contemplated herein. In addition to antibodies, aptamers that bind to an Occludin extracellular loop can be used to inhibit HCV infection. As used herein, an aptamer can comprise any DNA, RNA, oligonucleotide, or chemically modified oligonucleotide that binds to a target. Isolation and identification of aptamers has been disclosed (U.S. Pat. No. 5,582,981, U.S. Pat. No. 6,867,289, U.S. Pat. No. 7,179,894). Alternatively, recombinant binding proteins that bind an endogenous Occludin extracellular loop can be used to inhibit HCV infection. As used herein, "recombinant binding proteins" are any non-naturally occurring proteins obtained by recombinant DNA or polymerase chain reaction-mediated reactions that bind to a target. Recombinant binding proteins can comprise polypeptide binding regions of immunoglobulin heavy chains variable domains, immunoglobulin light chain variable domains, V.alpha./V.beta. domains of T cell receptor proteins, or combinations thereof. Isolation and identification of recombinant binding proteins has been disclosed (U.S. Pat. No. 6,010,884 and U.S. Pat. No. 6,297,053).

Blockage of HCV regions to inhibit HCV infection can also be effected by agents that mimic the region of Occludin extracellular loop that interacts with HCV. Without seeking to be limited by theory, contacting HCV with agents that mimic the critical region of an Occludin extracellular loop is expected to inhibit productive interactions of HCV with endogenous Occludin that permit cellular entry of HCV and HCV infection. These agents are expected to competitively inhibit interactions with HCV and endogenous Occludin. One advantage of Occludin extracellular loop mimicking agents is that they can be optimized such that their interactions with the critical regions of HCV are potentiated while their interactions with any other endogenous cellular ligands that recognize an endogenous Occludin extracellular loop are minimized. Optimization of Occludin mimicking agents is expected to provide for inhibition, prevention or mitigation of HCV infection while minimizing undesirable side effects.

In practicing any of the above referenced methods involving administration of HCV inhibitory, preventative or mitigating agents to a subject, it is contemplated that a variety of pharmaceutical compositions comprising these active agents can be administered by a variety of techniques. Such pharmaceutical compositions may be formulated in various ways known in the art for administration purposes. To prepare the pharmaceutical compositions of the present invention, an effective amount of the particular compound, in base or acid salt form, as the active ingredient is combined with one or more pharmaceutically acceptable carriers and delivery vehicles. Numerous pharmaceutically acceptable carriers and delivery vehicles exist that are readily accessible and well known in the art, which may be employed to generate the preparation desired (i.e., that permit administration of the pharmaceutical composition orally, topically, rectally, percutaneously, by parenteral injection, intranasally or by inhalation). Representative examples of pharmaceutically acceptable carriers and delivery vehicles include aluminum stearate, lecithin, serum proteins, such as human serum albumin; buffer substances such as the various phosphates, glycine, sorbic acid, potassium sorbate, partial glyceride mixtures of saturated vegetable fatty acids; water, salts or electrolytes, such as protamine sulfate, disodium hydrogen phosphate, potassium hydrogen phosphate, sodium chloride, and zinc salts; colloidal silica, magnesium trisilicate, polyvinyl pyrrolidone, cellulose-based substances, polyethylene glycol, sodium carboxymethylcellulose, polyarylates, waxes, polyethylene, polyoxypropylene-block polymers, polyethylene glycol and wool fat, and the like. The pharmacologic compositions described herein may further be prepared in unitary dosage form suitable for administration orally, percutaneously, by parenteral injection (including subcutaneous, intramuscular, intravenous and intradermal), topically, intranasally, by inhalation, or for application to a medical device, such as an implant, catheter, or other device. In preparing the compositions that permit administration of an oral dosage, for example, any of the pharmaceutically acceptable carriers known in the art may be used, such as water, glycols, oils, alcohols and the like in the case of carriers that permit oral delivery of liquid preparations such as suspensions, syrups, elixirs and solutions. When solid pharmaceutically acceptable carriers are desired that permit oral or rectal administration, starches, sugars, kaolin, lubricants, binders, cellulose and its derivatives, and disintegrating agents and the like may be used to prepare, for example, powders, pills, capsules and tablets. For pharmaceutically acceptable carriers that permit parenteral administration, the pharmaceutically acceptable carriers often comprise sterile water, which may be supplemented with various solutes to, for example, increase solubility. Injectable solutions may be prepared in which the pharmaceutically acceptable carrier comprises saline solution, glucose solution, or a mixture thereof, which may include certain well-known anti-oxidants, buffers, bacteriostats, and other solutes that render the formulation isotonic with the blood of the intended patient.

A variety of in vitro and cell based assays that provide for identification of compounds or agents that inhibit interactions of HCV with Occludin are contemplated herein. Inhibition of HCV interactions with Occludin can be used to inhibit, mitigate or prevent infection of a subject with any major HCV genotype, subtype, isolate, and/or quasispecie. HCV genotypes include, but are not limited to, genotypes 1, 2, 3, 4, 5 and 6 and HCV subtypes include, but are not limited to, subtypes Ia, Ib, 2a, 2b, 2c, 3a, 4a-4f, 5a and 6a. Furthermore, those skilled in the art will appreciate that agents or compounds that interact with any region of Occludin can disrupt Occludin functions that provide for HCV entry. In vitro assays comprise any assay wherein binding, interaction or association of a recombinant Occludin protein with HCV or components of HCV is determined. It is understood that the binding of recombinant Occludin with HCV or components of HCV can be either direct or indirect. Indirect binding would entail binding of Occludin to HCV through an intermediary. Recombinant Occludin protein can be used in the in vitro binding or interaction assays in either a soluble form or in insoluble forms such as liposomes. Other insoluble forms that can be used in binding assays include forms where the recombinant Occludin protein is coupled to a solid support. Solid supports include beads, microtiter plates, column matrices, or any other materials suitable for immobilizing proteins for binding assays. Soluble forms of the recombinant Occludin can further comprise sequences that facilitate solubility, detection and/or retention. Sequences that can facilitate solubility include, but are not limited to, sequences from glutathione-S-transferases or E. coli maltose binding proteins. Sequences that facilitate detection include any reporter protein, any epitope or any protein-binding domain. Those skilled in the art will appreciate that any of the foregoing sequences that promote solubility or detection can also facilitate retention. Retention is typically used in binding assays to associate the protein or protein ligand to a solid support. The recombinant protein can also further comprise additional sequences for retention such as FLAG™ epitopes (Stratagene, La Jolla, Calif., USA), myc epitopes, histidine tags and the like.

Binding or interaction of the recombinant Occludin protein to any HCV or HCV derived material such as HCV, HCVcc, HCVpp, semi-purified HCV components, purified HCV proteins or recombinant HCV protein(s) can be determined in the methods contemplated herein. Binding or interaction of recombinant Occludin to HCV EI and E2 proteins is specifically contemplated.

Such binding may be either direct or indirect. Either the recombinant Occludin or the HCV or HCV derived materials can be detectably labeled to facilitate the binding assay. In certain embodiments, the recombinant Occludin and the HCV or HCV derived materials are labeled with distinct detectable labels permitting simultaneous detection of each. In binding assays, the recombinant Occludin protein is typically contacted by the HCV or HCV derived material, subjected to some form of buffer exchange, and binding determined. Binding may be determined by any suitable technique or combination of techniques, including but not limited to, detection of a bound label, surface plasmon resonance, or scintillation proximity assays. Those skilled in the art will recognize that the method by which the Occludin sequences are presented on the extracellular surface of the cell is not critical, so long as those sequences are presented in a manner that permits HCV interaction.

In certain embodiments of the method, the cell expressing the recombinant, membrane bound extracellular Occludin amino acid residues is contacted by any of an HCV envelope protein, a cell expressing HCV envelope proteins EI and E2, an HCV pseudotyped retroviral particle, an HCVcc particle, an ex vivo HCVcc particle or HCV. When the cell expressing the recombinant Occludin is contacted by an HCV envelope protein(s), one can determine if binding of the envelope protein(s) is inhibited by a compound or agent by monitoring the presence or absence of the envelope protein following a buffer exchange. Such binding analyses are facilitated by providing detectably labeled envelope proteins. Binding of cells expressing envelope proteins, HCVpp, HCVcc, ex vivo HCVcc, or HCV to the cell expressing the recombinant Occludin can also be monitored in the manner described for binding of envelope proteins. Infection by HCVpp or HCVcc can also be monitored by the use of reporter genes encoded by these species, which can be assayed for in cells following exposure to the agents or compounds.

The use of recombinant Occludin proteins in in vitro assays that model other aspects of Occludin-mediated HCV entry into cells is also contemplated. Such assays would involve use of biochemical fractions from HCV, HCVcc, ex vivo HCV, HCVpp, recombinant cells expressing HCV envelope protein(s), reconstituted liposomes containing HCV components and other fractions or reconstituted materials derived from recombinant Occludin expressing cells.

Interactions of HCV with Occludin that result in entry of HCV into the cell can also be assayed to identify compounds or agents that interfere with any aspect of that process. Productive interaction or fusion of cells expressing envelope proteins, HCVpp, HCVcc, ex vivo HCVcc, or HCV to the cell expressing the recombinant Occludin can also be assayed by techniques that monitor transfer of proteins or nucleic acids from the cells expressing envelope proteins, HCVpp, HCVcc, ex vivo HCVcc, or HCV to the cell expressing the recombinant Occludin. In certain embodiments, transfer of a reporter gene is monitored. When the reporter is transferred from HCVpp or any other suitable viral vector, the reporter will be expressed only upon entry into the cell expressing the recombinant Occludin protein. When the reporter is present in a distinct cell that fuses to the cell expressing the recombinant Occludin protein, the reporter gene will only be expressed when the cells fuse and the reporter is exposed to a factor in the cell expressing the recombinant Occludin protein. Methods that provide for expression of a reporter upon cell fusion include, but are not limited to, operable linkage of the reporter to a promoter that is regulated by a trans-acting transcription factor present in the host cell. Entry of HCV, HCVcc, or ex vivo HCVcc can also be determined by any hybridization- or polymerase chain reaction-based method for measuring the associated HCV RNA. Entry of replication-competent HCV RNA into cells that permit HCV RNA replication results in a substantial signal amplification due to HCV RNA replication. When quantitating HCV RNA by use of a quantitative reverse-transcriptase Polymerase Chain Reaction (qRT-PCR), the HCV-derived PCR product can be detected by use of any labeled polynucleotide probes, by use of an intercalating dye such as ethidium bromide or SYBR green, use of a hybridization probe containing a fluorophore and a quencher such that emission from the fluorophore is only detected when the fluorophore is released by the 5' nuclease activity of the polymerase used in the PCR reaction (i.e., a TaqMan™ reaction; Applied Biosystems, Foster City, Calif.) or use of methods where the fluorophore and quencher are displaced by polymerase mediated synthesis of the complementary strand (i.e., Scorpion™ or Molecular Beacon™ probes). Various methods for conducting qRT-PCR analysis to quantitate mRNA levels are well characterized (Bustin, S. A.; Journal of Molecular Endocrinology 29, 23, 2002). Fluorescent probes that are activated by the action of enzymes that recognize mismatched nucleic acid complexes (i.e., Invader™, Third Wave Technologies, Madison, Wis.) can also be used to quantitate RNA. Those skilled in the art will also understand that RNA quantitation techniques such as Quantitative Nucleic Acid Sequence Based Amplification (Q-NASBA™) can be used to quantitate TIC807 protein-encoding mRNA and identify expressing plants. Commercially available kits for quantitating HCV RNA include the COB AS™ TaqMan HCV Test (TaqMan HCV; Roche Molecular Systems Inc., Branchburg, N.J.). HCVcc that comprise reporter genes are also available, thus allowing the quantification of infection following challenge similarly to the methods described for HCVpp.

To identify agents that inhibit interactions of HCV regions with Occludin, a variety of different libraries can be queried. Bacteriophage libraries comprising phage vectors that display antibody antigen recognition regions are one potential source of Occludin recognition agents and have been described in U.S. Pat. No. 6,265,150. Methods for generating libraries of antigen-combining proteins of high diversity are described in U.S. Pat. No. 5,780,225 and U.S. Pat. No. 6,303,313. Methods of using libraries to obtain antigen recognition regions are also described in U.S. Pat. No. 5,395,750. Methods of obtaining a nucleic acid encoding a binding protein having a proteinaceous binding domain that binds a predetermined target material are described in U.S. Pat. No. 5,223,409. Yeast antibody display libraries can also be used to obtain antigen recognition regions and as described in U.S. Pat. No. 6,300,065. Those skilled in the art will recognize that such antigen recognition sequences can subsequently be isolated from the recombinant phage, bacterial or yeast vector and reengineered into a synthetic antibody appropriate for use in subjects. Reengineering of these recognition domains into humanized antibodies is particularly contemplated.

Kits for Identifying Compounds or Agent that Prevent or Mitigate Interaction of a Region of a Hepatitis C Virus with a Region of a Occludin Protein.

In the particular embodiments contemplated herein, the methods and kits detect interactions of a region of HCV with an Occludin protein.

A kit may contain any of: i) a recombinant protein comprising an Occludin Protein or conservative amino acid substitutions thereof, or ii) a recombinant vector that provides for expression of an Occludin protein expressing an extra-cellular loop, or iii) a cell comprising said recombinant vector and instructions for using the kit. The kit may also contain reagent(s) for detecting an interaction between a sample comprising HCV, HCVcc, HCVpp, HCV envelope proteins and the aforementioned recombinant proteins, vectors or cells comprising an Occludin protein. The provided reagent(s) can be radio-, spectrophotometrically-, fluorescently- or enzymatically-labeled. The provided reagents can also be detectably labeled by other materials. The provided reagents may include a substrate that is converted to a product that can be detected by spectrophotometry, luminometry, or fluorescence. The kit can contain a known radiolabeled or haptenlabeled agent capable of binding or interacting with an antibody of the present invention.

The reagent(s) of the kit may be provided as a liquid solution, attached or otherwise deposited in or on a solid support or as a dried powder. Preferably, when the reagent(s) are provided in a liquid solution, the liquid solution is an aqueous solution. Preferably, when the reagent(s) provided are attached to, or otherwise deposited on a solid support, the solid support can be chromatography media, a test plate having a plurality of wells, or a microscope slide. When the reagent(s) provided are a dry powder, the powder can be reconstituted by the addition of a suitable solvent, that may be provided.

The container will generally include a vial into which the recombinant protein, recombinant vector, cells or detection reagent may be placed, and preferably suitably aliquotted. The kits of the present invention will also typically include a means for containing the recombinant protein, recombinant vector and/or cells in a container in close confinement for commercial sale. Such containers may include injection or blow-molded plastic containers into which the desired vials are retained. However, it is also contemplated that such kits may be assembled not for commercial sale, but for internal use within a research group. Thus the usefulness of such kits is not restricted to commercial sales. The instructions for the kit may either be enclosed in the kit or provided by way of reference to a external or internal website or other internal or external document or reference.

The embodiments were chosen and described in order to best explain the principles of the invention and its practical application to thereby enable others skilled in the art to best utilize the invention in various embodiments and with various modifications as are suited to the particular use contemplated.

EXAMPLES

Example 1

Supplemental Material and Methods

Cells 293T, 786-O, AML12, H2.35, Hep3B, Hepa1.6, HepG2, Huh-7.5, L929, NIH3T3, STO6 and TZM cells were maintained in DMEM with 10% fetal bovine serum (FBS). CHO cells were maintained in DMEM/F-12 with 10% FBS. HepG2 were grown on collagen coated plastic.

Antibodies and Reagents

A mouse monoclonal antibody against OCLN (clone OC-3F10) was purchased from Zymed Laboratories (San Francisco, Calif.). Mouse anti-CD81 1.3.3.22 was obtained from Santa Cruz Biotechnology (Santa Cruz, Calif.). Purified mouse IgG1 was from BD Pharmingen (Franklin Lakes, N.J.). The mouse anti-NS5A antibody 9E10 (15) and human anti-SR-BI antibody C167 (5) have previously been described. Alexa Fluor488 conjugated anti-mouse IgG secondary antibodies were obtained from Invitrogen (Carlsbad, Calif.) and R-phyco-erythrin (PE) goat anti-mouse IgG secondary antibodies were obtained from Jackson ImmunoResearch Laboratories, Inc. (West Grove, Pa.). Anti human IgG4 antibodies and streptavidin APC were obtained from BD Biosciences Pharmingen (San Diego, Calif.).

DNA Constructs

As described below, an NIH3T3 clone expressing human CD81, SR-BI, and CLDN1 was derived by progressive transduction with VSVG-packaged proviruses followed by cell sorting. These proviral genomes were based on the pTRIP (23, 27) self-inactivating lentiviral provirus that does not express HIV proteins, but instead employs an internal CMV promoter to express cloned genes. Previously described TRIP lentiviral plasmids include TRIP-CD81 (28), and TRIP-mCherry-CLDN1 (11). TRIP-hSR-BI was cloned by amplifying the human SR-BI orf with primers 5' GAC GAG CTG TAC AGA TCT AGA ATG GGC TGC TCC GCC AAA GCG CGC TGG (SEQ ID NO: 1) and 5' G GCG GTC GAC CTA CAG TTT TGC TTC CTG CAG CAC AGA (SEQ ID NO: 2). This product was cloned as a BglII/SalI fragment into BamHI/XhoI digested TRIP-GFP, thus replacing the GFP coding sequence. TRIP-mSR-BI, was constructed by amplifying the mouse SR-BI orf with primers 5' GAC GAG CTG TAC AGA TCT AGA ATG GGC GGC AGC TCC AGG GCG CGC TGG (SEQ ID NO: 3) and 5' GGCG CTC GAG CTA TAG CTT GGC TTC TTG CAG CAC CGT (SEQ ID NO: 4). This fragment was then cloned as a BglII/XhoI fragment into BamHI/XhoI digested TRIP-GFP, thus replacing the GFP coding sequence.

The CSGW and CSPW plasmids have been previously described (9). LMN8-hOCLN was created by cloning the rescued RT-PCR product with PmlI and SfiI into LMN8Sfillink (see description below). For amplification of human and mouse OCLN, expressed sequence tag (EST) clones (MGC IRAT Human 5179203 and LLAM 3658586, respectively) constructed by the Integrated Molecular Analysis of Genome Expression (I.M.A.G.E.) Consortium (image.llnl.gov) were obtained from the American Type Culture Collection (ATCC, Manassas, Va.). TRIP-hOCLN was constructed by amplifying the complete OCLN orf with primers 5' GAC GAG CTG TAC AGA TCT AGA ATG TCA TCC AGG CCT CTT GAA (SEQ ID NO: 5) and 5' GGGG CTC-GAG CTA TGT TTT CTG TCT ATC ATA GTC (SEQ ID NO: 6) and this PCR product was cloned as a partial BglII/XhoI fragment into pTRIP at the BamHI and XhoI sites. The same PCR product was cloned as a partial BsrGI/XhoI fragment into TRIP-GFP, creating a GFP-hOCLN fusion termed TRIP-GFP-hOCLN. In most derivatives of this plasmid the BglII site in the hOCLN orf was disrupted by inserting silent mutants by overlapping PCR (AGA TCT GAA to AGg TCc GAA), facilitating cloning. As an alternative to GFP, the TRIP-Venus fluorescent protein lentiviral expression plasmid was created by amplifying the Venus (18) orf (provided by Atsushi Miyawaki, RIKEN, Saitama, Japan) with the primers 5' GGGG GGA TCC GGA ATG GTG AGC AAG GGC GAG GAG CTG TTC (SEQ ID NO: 7) and 5' GGG CTCGAG TTA CTT GTA GAG CTC GTC CAT GCC GAG AGT GAT (SEQ ID NO: 8). The resulting product was cloned as a BamHI/XhoI digested fragment into pTRIP-GFP digested with the same enzymes. TRIP-Venus-hOCLN was constructed by cloning the above hOCLN PCR product as a partial BsrGI/XhoI fragment into TRIP-Venus. TRIP-mOCLN was constructed by amplifying the mouse OCLN orf with the primers 5' GAC GAG CTG TAC AGA TCT AGA ATG TCC GTG AGG CCT TTT GAA AGT CCA (SEQ ID NO: 9) and 5' GGGG CTCGAG CTA AGG TTT CCG TCT GTC ATA ATC (SEQ ID NO: 10) (an internal BglII site was disrupted by silent mutaganesis, ATA AGA TCT GGA (SEQ ID NO: 11) to ATA AGg TCc GGA (SEQ ID NO: 12)). This product was cloned as a BglII/XhoI fragment into the BamHI/XhoI sites of TRIP-GFP, and as a partial BsrGI/XhoI fragment into like digested TRIP-GFP, to create TRIP-GFP-mOCLN, and TRIP-Venus, to create TRIP-Venus-mOCLN. Mouse/human chimaeras were created in the TRIP-Venus context by overlapping PCR amplification, as previously described for the construction of CLDN1/CLDN7 chimaeras (11). Identical methods and primers that were used to create TRIP-Venus were used to construct a lentiviral vector expressing the Cerulean fluorescent protein (21), termed TRIP-Cerulean. A NdeI/BsrGI fragment from this plasmid was cloned in place of the GFP orf in TRIP-GFP-hCLDN1 and TRIP-GFP-mCLDN1 (11) to create TRIP-Cerulean-hCLDN1 and TRIP-Cerulean-mCLDN1.

TRIP-mCherry-hCD81, which expresses a fusion of the mCherry fluorescent protein at the N-terminus of human CD81, was constructed by amplifying the CD81 orf from TRIP-hCD81 (13) with the primers 5' GAG CTG TAC AAG GGA TCC GTC ATG GGA GTG GAG GGC TGC ACC AAG TGC ATC (SEQ ID NO: 13) and 5' GGGG CTCGAG TCA GTA CAC GGA GCT GTT CCG GAT GCC ACA (SEQ ID NO: 14), which was cloned as a BsrGI/XhoI digested fragment into TRIP-mCherry-CLDN1 (11). TRIP-mCherry-mCD81, expressing mouse CD81, was amplified with the same primers using TRIP-mCD81 (13) as template and cloned in an identical manner.

The retroviral Huh-7.5 cell cDNA library was constructed essentially as previously described (11), except the cDNA inserts were cloned into a MLV based proviral vector, termed LMN8Sfillink (gift from Paul D. Bieniasz, The Aaron Diamond AIDS Research Center, The Rockefeller University) instead of the HIV-1 based pV1 vector. LMN8Sfillink is based on the pBMN-Z MLV provirus, which is an MLV genome containing retroviral LTRs and packaging signal; it does not express any viral proteins and instead encodes the LacZ gene. To generate LMN8, the LacZ gene was replaced with two Sfil sites suitable for cloning of cDNA according to the SMART cDNA Library Construction Kit (Clontech, Mountain View, Calif.). The final LMN8 Huh7.5 cDNA library contained $4 \times 10^7$ clones, 65% of which had inserts averaging 1,300 bp in size. LMN8GFP is a variation of this plasmid, where the EGFP gene was inserted at the Sfil sites of LMN8Sfillink.

Pseudoparticle Generation and Infection Assays

All pseudoparticles were generated by co-transfection of plasmids encoding (1) a provirus containing the desired reporter gene or transgene, (2) either MLV or HIV gag-pol and (3) an appropriate envelope glycoprotein. Unless otherwise noted HCVpp used in this study were generated using the H77 E1E2 sequence (residues 170-746) (12). Other E1E2 sequences (Con1, OH8, S52, ED43, SA13) used for HCVpp generation have been described previously (17). One day prior to transfection $8 \times 10^5$ 293T cells were seeded in a 35 mm² dish. A total of 1.5 µg DNA was transfected using 6 µl FuGENE 6 (Roche Applied Science, Indianapolis, Ind.) and media was replaced after 6 h. Supernatants were harvested at 24 h, 48 h and 72 h after transfection, pooled and filtered (0.45 µm pore size). The following plasmid combinations and ratios (by weight) were used: To generate GFP or puromycin reporter HCVpp and controls, plasmids encoding (1) a provirus encoding the respective reporter gene (CSGW or CSPW), (2) HIV gag-pol and (3) either HCV strain H77 E1E2, VSV-G or empty vector were transfected at a 1:1:4 ratio. To generate pseudoparticles for transgene delivery, plasmids encoding (1) a pTRIP provirus containing the desired transgene, (2) HIV gag-pol and (3) VSV-G were co-transfected at a 7:7:1 ratio. For packaging of the cDNA library, plasmids encoding (1) either a LMN8 provirus containing the desired transgene, (2) MLV gag-pol and (3) VSVG were co-transfected at a 7:7:1 ratio. (For details on pseudoparticle generation in the context of cyclic repackaging see below.) All transductions and infection assays using pseudoparticles were performed in the presence of 4 µg/ml polybrene.

For infection assays with GFP reporter HCVpp, $2 \times 10^4$ cells were plated in 48-well-plates. The next day the cells were infected with pseudoparticles for 6 h. The media was changed and cells were further cultured for 72 h prior to harvesting and fixation with 0.5% w/v paraformaldehyde. GFP expression was quantified using a LSR2 flow cytometer (Becton Dickinson, Franklin Lakes, N.J.). The background GFP signal from non-enveloped pseudoparticles (Env-pp) was subtracted from the VSVGpp and HCVpp signals, the HCVpp signal was then normalized to VSVGpp infectivity [(HCVpp-NE)/(VSVG-NE)] and then normalized to HCVpp infectivity in Huh-7.5 cells to allow for cross-experimental comparison. Except where noted otherwise, results of infection experiments are the mean of greater than three independent infections, and, in the case of the chimaera and mutant OCLN analysis, of at least two independently transduced populations. Errors bars represent the standard deviation of the mean.

Generation of NIH3T3 Clones Stably Expressing hCD81, hSRBI and/or hCLDN1

NIH3T3 mouse embryonic fibroblasts were transduced with VSVGpp encoding TRIP lentivirus expressed human CD81, SR-BI or N-terminally-mCherry-tagged CLDN1. Expression was visualized using antibodies against human CD81 in combination with an Alexa-488 conjugated goat-anti-mouse-IgG antibodies against human SR-BI in combination with a biotinylated anti-human IgG4 and streptavidin APC or by direct mCherry fluorescence detection. Clonal populations were generated by single cell sorting using an FACS Aria cell sorter (Becton Dickinson, Franklin Lakes, N.J.) and clones with similar expression levels as Huh-7.5 cells were selected for the next round of transduction. This procedure was repeated to obtain cell clones stably expressing human homologues of CD81, SR-BI and CLDN1 in single, double and triple combinations. The final triple transduced clone expressing all three human proteins was designated NIH3T3 N3xF26.

Multicolour-Flow Cytometry

In order to directly correlate expression of lentivirus-delivered transgenes and HCVpp permissiveness, we used multi-colour flow cytometry. Fluorescence from HCVpp infection (GFP), CD81 (mCherry), SR-BI (APC staining), CLDN1 (Cerulean) and OCLN (Venus) was distinguished on a LSR2 flow cytometer (Becton Dickinson, Franklin Lakes, N.J.).

cDNA Library Screening and Cyclic Packaging Rescue

A schematic overview of the iterative library screening approach is provided in FIG. 4A. cDNA cloned into the retroviral LMN8 vector was packaged into MLV-based pseudoparticles bearing the VSV-G glycoprotein as described above. Since the LMN8 vector does not encode a reporter gene, the titer of pseudoparticles carrying the human cDNA library was estimated by extrapolating the titer from LMN8-EGFP pseudoparticles that were generated in parallel. The estimated titers were then used to approximate the effective titer of the library virus on the cell line of interest, based on the measurable infectivity of GFP on the cell line of interest. VSVGpp carrying the LMN8-library were then used to transduce NIH3T3 expressing human CD81, SR-BI and mCherry-CLDN1 (N3xF26) cells at a multiplicity of infection of about 1. Approximately $1 \times 10^7$ cells were transduced for the first round of screening; lower numbers were used in subsequent rounds. Cells expressing the library were challenged with HCVpp carrying a puromycin (CSPW) selection marker, with antibiotic selection was applied after 48 h. Surviving cell clones were pooled and transfected with MLV gag-pol and VSV-G to re-package the LMN8/cDNA genomes present in these cells into pseudoparticles and deliver them to a naïve population of N3xF26 cells for additional rounds of selection. We performed a total of three selection steps, i.e. library delivery, infection with HCVpp encoding puromycin resistance followed by selection with puromycin. After each selection step a fraction of the population was challenged with GFP reporter Env-pp, HCVpp and VSVGpp to monitor for the appearance of an HCVpp-susceptible subpopulation (FIG. 4B). Single cell clones of the final triple selected population were derived and the genomic DNA from these clones was prepared with the DNeasy tissue kit (QIAGEN, Valencia, Calif.) according to the manufacturer's protocol. The cDNA LMN8 inserts were amplified with primers specific for the LMN8 sequence flanking the cDNA cloning site, 5' ACCGC-CCTCAAAGTAGAC (SEQ ID NO: 15) and 5' GCTTGC-CAAACCTACAGG (SEQ ID NO: 16). These PCR products were TA cloned and sequenced.

HCVcc Generation and Infections

Jc1 FLAG(p7-nsGluc2A), used for the experiments in this study was previously described (16). HCVcc was generated as previously reported (15). HCVcc was collected from supernatants 48-72 h after transfection. Infectious units (as median tissue culture infective dose [TCID50]) were quantified by limiting dilution titration on naive Huh-7.5 cells. For infection experiments Huh-7.5 cells were seeded in 48 well plates. The next day HCVcc containing supernatant was applied and, after 72 h, infection was detected by staining for NS5A with the 9E10 anti-NS5A as primary and a PE-conjugated goat anti-mouse secondary antibody; the signal was quantified by flow-cytometrical analysis.

RT-PCR Quantification of HCV Entry Factors

To quantify expression of HCV entry factors in various cell lines, total RNA was isolated using a QIAGEN RNA isolation kit (Valencia, Calif.). cDNA was synthesized according to manufacturers instructions using a RETROSCRIPT FIRST STRAND SYNTHESIS Kit (Ambion, Austin, Tex.). Quantitative PCR was performed with a Light Cycler LC480 machine (Roche Applied Science, Indianapolis, Ind.) using a SYBR green Quantitect Primer Assay (QIAGEN) in combination with the following gene specific primer pairs:

| Gene  | Forward primer                       | Reverse primer                        |
|-------|--------------------------------------|---------------------------------------|
| CD81  | ACCTCCTGTATCTGGAGCTGG (SEQ ID NO: 17) | TTGGCGATCTGGTCCTTGTTG (SEQ ID NO: 18) |
| SR-BI | TCGCAGGCATTGGACAAACT (SEQ ID NO: 19) | CTCCTTATCCTTTGAGCCCTTTT (SEQ ID NO: 20) |
| CLDN1 | GTGGAGGATTTACTCCTATGCCG (SEQ ID NO: 21) | ATCAAGGCACGGGTTGCTT (SEQ ID NO: 22) |
| OCLN  | TCAAACCGAATCATTATGCACCA (SEQ ID NO: 23) | AGATGGCAATGCACATCACAA (SEQ ID NO: 24) |
| GAPDH | AGGTCGGTGTGAACGGATTTG (SEQ ID NO: 25) | TGTAGACCATGTAGTTGAGGTCA (SEQ ID NO: 26) |

Analysis of HCV Entry Receptor Expression in CHO Cells and Hamster Liver

For the analysis of HCV entry receptor expression in CHO cells and hamster liver the following PCR primers were used to amplify the hamster specific genes:

| Gene  | Forward primer                       | Reverse primer                        |
|-------|--------------------------------------|---------------------------------------|
| CD81  | GTGGAGGGCTGCACCAAAT (SEQ ID NO: 27)  | GGCGCAACCACAGAGCCACA (SEQ ID NO: 28)  |
| SR-BI | TTTGGAGTGGTAGTAAAAGGGC (SEQ ID NO: 29) | TGACATCAGAGACTCAGAGTAG (SEQ ID NO: 30) |
| CLDN1 | AGATGTGGATGGCTGTCATTGG (SEQ ID NO: 31) | AAGAGCAAGAAAGTAGGGCACCTC (SEQ ID NO: 32) |
| OCLN  | CAGCAAAGGTTTCCTGTTGGC (SEQ ID NO: 33) | TGGGCAGTTGGGTTGACTCC (SEQ ID NO: 34)  |
| GAPDH | GTATTGGACGCCTGGTTACCA (SEQ ID NO: 35) | GGTAGAGTCATACTGGAACATGTAC (SEQ ID NO: 36) |

Analysis of HCV Entry Receptor Expression in Mouse Cells and Mouse Liver

For the analysis of HCV entry receptor expression in mouse cells and mouse liver the following PCR primers were used to amplify the mouse specific genes:

| Gene | Forward primer | Reverse primer |
|---|---|---|
| CD81 | GTGGAGGGCTGCACCAAAT (SEQ ID NO: 37) | GACGCAACCACAGAGCTACA (SEQ ID NO: 38) |
| SR-BI | TTTGGAGTGGTAGTAAAAAGGGC (SEQ ID NO: 39) | TGACATCAGGGACTCAGAGTAG (SEQ ID NO: 40) |
| CLDN1 | AAGTCTTCGACTCCTTGCTGA (SEQ ID NO: 41) | TGTCGCCAGACCTGAAATTAAAA (SEQ ID NO: 42) |
| OCLN | TTTTTGCTGTGAAAACCCGAAG (SEQ ID NO: 43) | CTGTCAACTCTTTCCGCATAGT (SEQ ID NO: 44) |
| GAPDH | AATCCCATCACCATCTTCC (SEQ ID NO: 45) | CATCACGCCACAGTTTCC (SEQ ID NO: 46) |

RNA Interference

Pools of siRNAs directed against human CD81, human OCLN and non-targeting siRNAs (ON-TARGETplus SMARTpools) were purchased from Dharmacon (Lafayette, Colo.). Huh-7.5 and Hep3B cells were reverse transfected according to manufacturers instructions. Briefly, for transfection 0.5 µl RNAiMAX (Invitrogen, Carlsbad, Calif.) and 50 pmol siRNA were used per well. $1 \times 10^4$ cells per well were seeded with the transfection mix in 48-well plates. At 48 h post-transfection and seeding, protein expression was flow-cytometrically determined and infection assays were performed.

Occludin Gen Bank Accession Number

Human-NM_002538 14 Sep. 2008 (DNA sequence of SEQ ID NO:47; Protein Sequence of SEQ ID NO:48).

Statistical Analyses

All statistical analyses were performed using Prism4 software (GraphPad Software, San Diego, Calif.).

REFERENCES

1. Bartosch, B., J. Bukh, J. C. Meunier, C. Granier, R. E. Engle, W. C. Blackwelder, S. U. Emerson, F. L. Cosset, and R. H. Purcell. 2003. In vitro assay for neutralizing antibody to hepatitis C virus: evidence for broadly conserved neutralization epitopes. Proc Natl Acad Sci USA 100:14199-204.
2. Bartosch, B., J. Dubuisson, and F. L. Cosset. 2003. Infectious hepatitis C virus pseudo-particles containing functional E1-E2 envelope protein complexes. J Exp Med 197:633-642.
3. Blight, K. J., J. A. McKeating, and C. M. Rice. 2002. Highly permissive cell lines for hepatitis C virus genomic and subgenomic RNA replication. J. Virol. 76:13001-14.
4. Brazzoli, M., A. Bianchi, S. Filippini, A. Weiner, Q. Zhu, M. Pizza, and S. Crotta. 2008. CD81 is a central regulator of cellular events required for hepatitis C virus infection of human hepatocytes. J Virol 82:8316-29.
5. Catanese, M. T., R. Graziani, T. von Hahn, M. Moreau, T. Huby, G. Paonessa, C. Santini, A. Luzzago, C. M. Rice, R. Cortese, A. Vitelli, and A. Nicosia. 2007. High-avidity monoclonal antibodies against the human scavenger class B type I receptor efficiently block hepatitis C virus infection in the presence of high-density lipoprotein. J Virol 81:8063-71.
6. Chiba, H., M. Osanai, M. Murata, T. Kojima, and N. Sawada. 2008. Transmembrane proteins of tight junctions. Biochim Biophys Acta 1778:588-600.
7. Coyne, C. B., and J. M. Bergelson. 2006. Virus-induced Abl and Fyn kinase signals permit coxsackievirus entry through epithelial tight junctions. Cell 124:119-31.
8. Coyne, C. B., L. Shen, J. R. Turner, and J. M. Bergelson. 2007. Coxsackievirus entry across epithelial tight junctions requires occludin and the small GTPases Rab34 and Rab5. Cell Host Microbe 2:181-92.
9. Demaison, C., K. Parsley, G. Brouns, M. Scherr, K. Battmer, C. Kinnon, M. Grez, and A. J. Thrasher. 2002. High-level transduction and gene expression in hematopoietic repopulating cells using a human immunodeficiency [correction of imunodeficiency] virus type 1-based lentiviral vector containing an internal spleen focus forming virus promoter. Hum Gene Ther 13:803-13.
10. Drummer, H. E., A. Maerz, and P. Poumbourios. 2003. Cell surface expression of functional hepatitis C virus E1 and E2 glycoproteins. FEBS Lett 546:385-90.
11. Evans, M. J., T. von Hahn, D. M. Tscherne, A. J. Syder, M. Panis, B. Wolk, T. Hatziioannou, J. A. McKeating, P. D. Bieniasz, and C. M. Rice. 2007. Claudin-1 is a hepatitis C virus co-receptor required for a late step in entry. Nature.
12. Flint, M., C. Logvinoff, C. M. Rice, and J. A. McKeating. 2004. Characterization of infectious retroviral pseudotype particles bearing hepatitis C virus glycoproteins. J Virol 78:6875-82.
13. Flint, M., T. von Hahn, J. Zhang, M. Farquhar, C. T. Jones, P. Balfe, C. M. Rice, and J. A. McKeating. 2006. Diverse CD81 proteins support hepatitis C virus infection. J Virol 80:11331-42.
14. Hsu, M., J. Zhang, M. Flint, C. Logvinoff, C. Cheng-Mayer, C. M. Rice, and J. A. McKeating. 2003. Hepatitis C virus glycoproteins mediate pH-dependent cell entry of pseudotyped retroviral particles. Proc. Natl. Acad. Sci. USA 100:7271-76.
15. Lindenbach, B. D., M. J. Evans, A. J. Syder, B. Wolk, T. L. Tellinghuisen, C. C. Liu, T. Maruyama, R. O. Hynes, D. R. Burton, J. A. McKeating, and C. M. Rice. 2005. Complete Replication of Hepatitis C Virus in Cell Culture. Science 309:623-6.
16. Marukian, S., C. T. Jones, L. Andrus, M. J. Evans, K. D. Ritola, E. D. Charles, C. M. Rice, and L. D. Dustin. in press (2008). Cell Culture-Produced Hepatitis C Virus Does Not Infect Peripheral Blood Mononuclear Cells. Hepatology.
17. McKeating, J. A., L. Q. Zhang, C. Logvinoff, M. Flint, J. Zhang, J. Yu, D. Butera, D. D. Ho, L. B. Dustin, C. M. Rice, and P. Balfe. 2004. Diverse hepatitis C virus glycoproteins mediate viral infection in a CD81-dependent manner. J Virol 78:8496-505.
18. Nagai, T., K. Ibata, E. S. Park, M. Kubota, K. Mikoshiba, and A. Miyawaki. 2002. A variant of yellow fluorescent protein with fast and efficient maturation for cell-biological applications. Nat Biotechnol 20:87-90.
19. Paris, L., L. Tonutti, C. Vannini, and G. Bazzoni. 2008. Structural organization of the tight junctions. Biochim Biophys Acta 1778:646-59.
20. Pileri, P., Y. Uematsu, S. Compagnoli, G. Galli, F. Falugi, R. Petracca, A. J. Weiner, M. Houghton, D. Rosa, G. Grandi, and S. Abrignani. 1998. Binding of hepatitis C virus to CD81. Science 282:938-941.
21: Rizzo, M. A., G. H. Springer, B. Granada, and D. W. Piston. 2004. An improved cyan fluorescent protein variant useful for FRET. Nat Biotechnol 22:445-9.
22. Scarselli, E., H. Ansuini, R. Cerino, R. M. Roccasecca, S. Acali, G. Filocamo, C. Traboni, A. Nicosia, R. Cortese, and A. Vitelli. 2002. The human scavenger receptor class B type I is a novel candidate receptor for the hepatitis C virus. EMBO Journal 21:5017-25.
23. Sirven, A., E. Ravet, P. Charneau, V. Zennou, L. Coulombel, D. Guetard, F. Pflumio, and A. Dubart-Kupperschmitt. 2001. Enhanced transgene expression in cord blood CD34 (+)-derived hematopoietic cells, including developing T cells and NOD/SCID mouse repopulating cells, following transduction with modified trip lentiviral vectors. Mol Ther 3:438-48.
24. Uprichard, S., F. Chisari, and T. Wakita. 2005. Presented at the 12th International Symposium on Hepatitis C Virus and Related Viruses, Montreal, Canada, October 2-6.
25. Uprichard, S. L., J. Chung, F. V. Chisari, and T. Wakita. 2006. Replication of a hepatitis C virus replicon clone in mouse cells. Virol J 3:89.
26. von Hahn, T., and C. M. Rice. 2008. Hepatitis C virus entry. J Biol Chem 283:3689-93.
27. Zennou, V., C. Petit, D. Guetard, U. Nerhbass, L. Montagnier, and P. Charneau. 2000. HIV-1 genome nuclear import is mediated by a central DNA flap. Cell 101:173-85.
28. Zhang, J., G. Randall, A. Higginbottom, P. Monk, C. M. Rice, and J. A. McKeating. 2004. CD81 is required for hepatitis C virus glycoprotein-mediated viral infection. J Virol 78:1448-55.
29. Zhu, Q., J. T. Guo, and C. Seeger. 2003. Replication of hepatitis C virus subgenomes in nonhepatic epithelial and mouse hepatoma cells. J Virol 77:9204-10.

What is claimed is:

1. A transgenic animal having integrated in the genome of the animal a human Occludin transgene and a human CD81 transgene wherein expression of the transgenes render the animal permissive for Hepatitis C Virus (HCV) entry and wherein said animal is selected from the group consisting of a mouse and a rat.

2. The transgenic animal of claim 1, wherein said animal is a mouse.

* * * * *

```
                            SEQUENCE LISTING

<160> NUMBER OF SEQ ID NOS: 48

<210> SEQ ID NO 1
<211> LENGTH: 48
<212> TYPE: DNA
<213> ORGANISM: Artificial Sequence
<220> FEATURE:
<223> OTHER INFORMATION: Synthetic

<400> SEQUENCE: 1
gacgagctgt acagatctag aatgggctgc tccgccaaag cgcgctgg                48

<210> SEQ ID NO 2
<211> LENGTH: 37
<212> TYPE: DNA
<213> ORGANISM: Artificial Sequence
<220> FEATURE:
<223> OTHER INFORMATION: Synthetic

<400> SEQUENCE: 2
ggcggtcgac ctacagtttt gcttcctgca gcacaga                            37

<210> SEQ ID NO 3
<211> LENGTH: 48
<212> TYPE: DNA
<213> ORGANISM: Artificial Sequence
<220> FEATURE:
<223> OTHER INFORMATION: Synthetic

<400> SEQUENCE: 3
gacgagctgt acagatctag aatgggcggc agctccaggg cgcgctgg                48

<210> SEQ ID NO 4
<211> LENGTH: 37
<212> TYPE: DNA
<213> ORGANISM: Artificial Sequence
<220> FEATURE:
<223> OTHER INFORMATION: Synthetic

<400> SEQUENCE: 4
```
ggcgctcgag ctatagcttg gcttcttgca gcaccgt    37

<210> SEQ ID NO 5
<211> LENGTH: 42
<212> TYPE: DNA
<213> ORGANISM: Artificial Sequence
<220> FEATURE:
<223> OTHER INFORMATION: Synthetic

<400> SEQUENCE: 5
gacgagctgt acagatctag aatgtcatcc aggcctcttg aa    42

<210> SEQ ID NO 6
<211> LENGTH: 34
<212> TYPE: DNA
<213> ORGANISM: Artificial Sequence
<220> FEATURE:
<223> OTHER INFORMATION: Synthetic

<400> SEQUENCE: 6
ggggctcgag ctatgttttc tgtctatcat agtc    34

<210> SEQ ID NO 7
<211> LENGTH: 40
<212> TYPE: DNA
<213> ORGANISM: Artificial Sequence
<220> FEATURE:
<223> OTHER INFORMATION: Synthetic

<400> SEQUENCE: 7 gggggggatcc ggaatggtga gcaagggcga ggagctgttc    40

<210> SEQ ID NO 8
<211> LENGTH: 42
<212> TYPE: DNA
<213> ORGANISM: Artificial Sequence
<220> FEATURE:
<223> OTHER INFORMATION: Synthetic

<400> SEQUENCE: 8
gggctcgagt tacttgtaca gctcgtccat gccgagagtg at    42

<210> SEQ ID NO 9
<211> LENGTH: 48
<212> TYPE: DNA
<213> ORGANISM: Artificial Sequence
<220> FEATURE:
<223> OTHER INFORMATION: Synthetic

<400> SEQUENCE: 9
gacgagctgt acagatctag aatgtccgtg aggcctttg aaagtcca    48

<210> SEQ ID NO 10
<211> LENGTH: 34
<212> TYPE: DNA
<213> ORGANISM: Artificial Sequence
<220> FEATURE:
<223> OTHER INFORMATION: Synthetic

<400> SEQUENCE: 10
ggggctcgag ctaaggtttc cgtctgtcat aatc    34

<210> SEQ ID NO 11
<211> LENGTH: 12
<212> TYPE: DNA
<213> ORGANISM: Artificial Sequence

```
<220> FEATURE:
<223> OTHER INFORMATION: Synthetic

<400> SEQUENCE: 11
ataagatctg ga                                                           12

<210> SEQ ID NO 12
<211> LENGTH: 12
<212> TYPE: DNA
<213> ORGANISM: Artificial Sequence
<220> FEATURE:
<223> OTHER INFORMATION: Synthetic

<400> SEQUENCE: 12
ataaggtccg ga                                                           12

<210> SEQ ID NO 13
<211> LENGTH: 51
<212> TYPE: DNA
<213> ORGANISM: Artificial Sequence
<220> FEATURE:
<223> OTHER INFORMATION: Synthetic

<400> SEQUENCE: 13
gagctgtaca agggatccgt catgggagtg gagggctgca ccaagtgcat c                51

<210> SEQ ID NO 14
<211> LENGTH: 40
<212> TYPE: DNA
<213> ORGANISM: Artificial Sequence
<220> FEATURE:
<223> OTHER INFORMATION: Synthetic

<400> SEQUENCE: 14
ggggctcgag tcagtacacg gagctgttcc ggatgccaca                             40

<210> SEQ ID NO 15
<211> LENGTH: 18
<212> TYPE: DNA
<213> ORGANISM: Artificial Sequence
<220> FEATURE:
<223> OTHER INFORMATION: Synthetic

<400> SEQUENCE: 15
accgccctca aagtagac                                                     18

<210> SEQ ID NO 16
<211> LENGTH: 18
<212> TYPE: DNA
<213> ORGANISM: Artificial Sequence
<220> FEATURE:
<223> OTHER INFORMATION: Synthetic

<400> SEQUENCE: 16
gcttgccaaa cctacagg                                                     18

<210> SEQ ID NO 17
<211> LENGTH: 21
<212> TYPE: DNA
<213> ORGANISM: Artificial Sequence
<220> FEATURE:
<223> OTHER INFORMATION: Synthetic

<400> SEQUENCE: 17
acctcctgta tctggagctg g                                                 21
```

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
ttggcgatct ggtccttgtt g                                    21

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
tcgcaggcat tggacaaact                                      20

<210> SEQ ID NO 20
<211> LENGTH: 23
<212> TYPE: DNA
<213> ORGANISM: Artificial Sequence
<220> FEATURE:
<223> OTHER INFORMATION: Synthetic

<400> SEQUENCE: 20
ctccttatcc tttgagccct ttt                                  23

<210> SEQ ID NO 21
<211> LENGTH: 23
<212> TYPE: DNA
<213> ORGANISM: Artificial Sequence
<220> FEATURE:
<223> OTHER INFORMATION: Synthetic

<400> SEQUENCE: 21
gtggaggatt tactcctatg ccg                                  23

<210> SEQ ID NO 22
<211> LENGTH: 19
<212> TYPE: DNA
<213> ORGANISM: Artificial Sequence
<220> FEATURE:
<223> OTHER INFORMATION: Synthetic

<400> SEQUENCE: 22
atcaaggcac gggttgctt                                       19

<210> SEQ ID NO 23
<211> LENGTH: 23
<212> TYPE: DNA
<213> ORGANISM: Artificial Sequence
<220> FEATURE:
<223> OTHER INFORMATION: Synthetic

<400> SEQUENCE: 23
tcaaaccgaa tcattatgca cca                                  23

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
agatggcaat gcacatcaca a                                              21

<210> SEQ ID NO 25
<211> LENGTH: 21
<212> TYPE: DNA
<213> ORGANISM: Artificial Sequence
<220> FEATURE:
<223> OTHER INFORMATION: Synthetic

<400> SEQUENCE: 25
aggtcggtgt gaacggattt g                                              21

<210> SEQ ID NO 26
<211> LENGTH: 23
<212> TYPE: DNA
<213> ORGANISM: Artificial Sequence
<220> FEATURE:
<223> OTHER INFORMATION: Synthetic

<400> SEQUENCE: 26
tgtagaccat gtagttgagg tca                                            23

<210> SEQ ID NO 27
<211> LENGTH: 19
<212> TYPE: DNA
<213> ORGANISM: Artificial Sequence
<220> FEATURE:
<223> OTHER INFORMATION: Synthetic

<400> SEQUENCE: 27
gtggagggct gcaccaaat                                                 19

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
ggcgcaacca cagagccaca                                                20

<210> SEQ ID NO 29
<211> LENGTH: 23
<212> TYPE: DNA
<213> ORGANISM: Artificial Sequence
<220> FEATURE:
<223> OTHER INFORMATION: Synthetic

<400> SEQUENCE: 29
tttggagtgg tagtaaaaag ggc                                            23

<210> SEQ ID NO 30
<211> LENGTH: 22
<212> TYPE: DNA
<213> ORGANISM: Artificial Sequence
<220> FEATURE:
<223> OTHER INFORMATION: Synthetic

<400> SEQUENCE: 30
tgacatcaga gactcagagt ag                                             22

<210> SEQ ID NO 31

```
<211> LENGTH: 22
<212> TYPE: DNA
<213> ORGANISM: Artificial Sequence
<220> FEATURE:
<223> OTHER INFORMATION: Synthetic

<400> SEQUENCE: 31
agatgtggat ggctgtcatt gg                                          22

<210> SEQ ID NO 32
<211> LENGTH: 24
<212> TYPE: DNA
<213> ORGANISM: Artificial Sequence
<220> FEATURE:
<223> OTHER INFORMATION: Synthetic

<400> SEQUENCE: 32
aagagcaaga aagtagggca cctc                                        24

<210> SEQ ID NO 33
<211> LENGTH: 21
<212> TYPE: DNA
<213> ORGANISM: Artificial Sequence
<220> FEATURE:
<223> OTHER INFORMATION: Synthetic

<400> SEQUENCE: 33
cagcaaaggt ttcctgttgg c                                           21

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
tgggcagttg ggttgactcc                                             20

<210> SEQ ID NO 35
<211> LENGTH: 21
<212> TYPE: DNA
<213> ORGANISM: Artificial Sequence
<220> FEATURE:
<223> OTHER INFORMATION: Synthetic

<400> SEQUENCE: 35
gtattggacg cctggttacc a                                           21

<210> SEQ ID NO 36
<211> LENGTH: 25
<212> TYPE: DNA
<213> ORGANISM: Artificial Sequence
<220> FEATURE:
<223> OTHER INFORMATION: Synthetic

<400> SEQUENCE: 36
ggtagagtca tactggaaca tgtac                                       25

<210> SEQ ID NO 37
<211> LENGTH: 19
<212> TYPE: DNA
<213> ORGANISM: Artificial Sequence
<220> FEATURE:
<223> OTHER INFORMATION: Synthetic

<400> SEQUENCE: 37
```
gtggagggct gcaccaaat 19

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
gacgcaacca cagagctaca 20

<210> SEQ ID NO 39
<211> LENGTH: 23
<212> TYPE: DNA
<213> ORGANISM: Artificial Sequence
<220> FEATURE:
<223> OTHER INFORMATION: Synthetic

<400> SEQUENCE: 39
tttggagtgg tagtaaaaag ggc 23

<210> SEQ ID NO 40
<211> LENGTH: 22
<212> TYPE: DNA
<213> ORGANISM: Artificial Sequence
<220> FEATURE:
<223> OTHER INFORMATION: Synthetic

<400> SEQUENCE: 40
tgacatcagg gactcagagt ag 22

<210> SEQ ID NO 41
<211> LENGTH: 21
<212> TYPE: DNA
<213> ORGANISM: Artificial Sequence
<220> FEATURE:
<223> OTHER INFORMATION: Synthetic

<400> SEQUENCE: 41
aagtcttcga ctccttgctg a 21

<210> SEQ ID NO 42
<211> LENGTH: 23
<212> TYPE: DNA
<213> ORGANISM: Artificial Sequence
<220> FEATURE:
<223> OTHER INFORMATION: Synthetic

<400> SEQUENCE: 42
tgtcgccaga cctgaaatta aaa 23

<210> SEQ ID NO 43
<211> LENGTH: 22
<212> TYPE: DNA
<213> ORGANISM: Artificial Sequence
<220> FEATURE:
<223> OTHER INFORMATION: Synthetic

<400> SEQUENCE: 43
tttttgctgt gaaacccga ag 22

<210> SEQ ID NO 44
<211> LENGTH: 22
<212> TYPE: DNA

```
<213> ORGANISM: Artificial Sequence
<220> FEATURE:
<223> OTHER INFORMATION: Synthetic

<400> SEQUENCE: 44
ctgtcaactc tttccgcata gt                                              22

<210> SEQ ID NO 45
<211> LENGTH: 19
<212> TYPE: DNA
<213> ORGANISM: Artificial Sequence
<220> FEATURE:
<223> OTHER INFORMATION: Synthetic

<400> SEQUENCE: 45
aatcccatca ccatcttcc                                                  19

<210> SEQ ID NO 46
<211> LENGTH: 18
<212> TYPE: DNA
<213> ORGANISM: Artificial Sequence
<220> FEATURE:
<223> OTHER INFORMATION: Synthetic

<400> SEQUENCE: 46
catcacgcca cagtttcc                                                   18

<210> SEQ ID NO 47
<211> LENGTH: 2648
<212> TYPE: DNA
<213> ORGANISM: Homo sapiens

<400> SEQUENCE: 47
gcctctctcc atcagacacc ccaaggttcc atccgaagca ggcggagcac cgaacgcacc      60
ccggggtggt cagggacccc catccgtgct gccccctagg agcccgcgcc tctcctctgc     120
gccccgcctc tcgggccgca acatcgcgcg gttccttttaa cagcgcgctg gcagggtgtg     180
ggaagcagga ccgcgtcctc ccgcccccta ccatccgagt ttcaggtgaa ttggtcaccg     240
agggaggagg ccgacacacc acacctacac tcccgcgtcc acctctccct ccctgcttcc     300
tctggcggag gcggcaggaa ccgagagcca ggtccagagc gccgaggagc cggtctagga     360
cgcagcagat tggtttatct tggaagctaa agggcattgc tcatcctgaa gatcagctga     420
ccattgacaa tcagccatgt catccaggcc tcttgaaagt ccacctcctt acaggcctga     480
tgaattcaaa ccgaatcatt atgcaccaag caatgacata tatggtggag agatgcatgt     540
tcgaccaatg ctctctcagc cagcctactc tttttaccca gaagatgaaa ttcttcactt     600
ctacaaatgg acctctcctc caggagtgat tcggatcctg tctatgctca ttattgtgat     660
gtgcattgcc atctttgcct gtgtggcctc cacgcttgcc tgggacagag gctatggaac     720 ttcccttttta ggaggtagtg taggctaccc ttatggagga agtggctttg gtagctacgg     780
aagtggctat ggctatggct atggttatgg ctatggctac ggaggctata cagacccaag     840
agcagcaaag ggcttcatgt tggccatggc tgccttttgt ttcattgccg cgttggtgat     900
ctttgttacc agtgttataa gatctgaaat gtccagaaca agaagatact acttaagtgt     960
gataatagtg agtgctatcc tgggcatcat ggtgtttatt gccacaattg tctatataat    1020
gggagtgaac ccaactgctc agtcttctgg atctctatat ggttcacaaa tatatgccct    1080
ctgcaaccaa ttttatacac ctgcagctac tggactctac gtggatcagt atttgtatca    1140
ctactgtgtt gtggatcccc aggaggccat tgccattgta ctggggttca tgattattgt    1200
```

```
ggcttttgct ttaataattt tctttgctgt gaaaactcga agaaagatgg acaggtatga    1260
caagtccaat attttgtggg acaaggaaca catttatgat gagcagcccc ccaatgtcga    1320
ggagtgggtt aaaatgtgt ctgcaggcac acaggacgtg ccttcacccc catctgacta    1380
tgtggaaaga gttgacagtc ccatggcata ctcttccaat ggcaaagtga atgacaagcg    1440
gttttatcca gagtcttcct ataaatccac gccggttcct gaagtggttc aggagcttcc    1500
attaacttcg cctgtggatg acttcaggca gcctcgttac agcagcggtg gtaactttga    1560
gacaccttca aaagagcac ctgcaaaggg aagagcagga aggtcaaaga gaacagagca    1620
agatcactat gagacagact acacaactgg cggcgagtcc tgtgatgagc tggaggagga    1680
ctggatcagg gaatatccac ctatcacttc agatcaacaa agacaactgt acaagaggaa    1740
ttttgacact ggcctacagg aatacaagag cttacaatca gaacttgatg agatcaataa    1800
agaactctcc cgtttggata agaattgga tgactataga gaagaaagtg aagagtacat    1860
ggctgctgct gatgaataca atagactgaa gcaagtgaag ggatctgcag attacaaaag    1920
taagaagaat cattgcaagc agttaaagag caaattgtca cacatcaaga gatggttgg     1980 agactatgat agacagaaaa catagaaggc tgatgccaag ttgtttgaga aattaagtat    2040
ctgacatctc tgcaatcttc tcagaaggca aatgactttg gaccataacc ccggaagcca    2100
aacctctgtg agcatcacaa agttttggtt gctttaacat catcagtatt gaagcatttt    2160
ataaatcgct tttgataatc aactgggctg aacactccaa ttaaggattt tatgctttaa    2220
acattggttc ttgtattaag aatgaaatac tgtttgaggt ttttaagcct taaaggaagg    2280
ttctggtgtg aactaaactt tcacacccca gacgatgtct tcatacctac atgtatttgt    2340
ttgcataggt gatctcattt aatcctctca accaccttc agataactgt tatttataat    2400 cactttttc cacataagga aactgggttc ctgcaatgaa gtctctgaag tgaaactgct    2460
tgtttcctag cacacacttt tggttaagtc tgttttatga cttcattaat aataaattcc    2520 ctggccttc atattttagc tactatat gtgatgatct accagcctcc ctattttttt    2580
tctgttatat aaatggttaa aagaggtttt tcttaaataa taaagatcat gtaaagtaa     2640 aaaaaaaa                                                             2648
```

<210> SEQ ID NO 48
<211> LENGTH: 522
<212> TYPE: PRT
<213> ORGANISM: Homo sapiens

<400> SEQUENCE: 48

```
Met Ser Ser Arg Pro Leu Glu Ser Pro Pro Tyr Arg Pro Asp Glu
1               5                   10                  15

Phe Lys Pro Asn His Tyr Ala Pro Ser Asn Asp Ile Tyr Gly Gly Glu
            20                  25                  30

Met His Val Arg Pro Met Leu Ser Gln Pro Ala Tyr Ser Phe Tyr Pro
        35                  40                  45

Glu Asp Glu Ile Leu His Phe Tyr Lys Trp Thr Ser Pro Pro Gly Val
    50                  55                  60

Ile Arg Ile Leu Ser Met Leu Ile Val Met Cys Ile Ala Ile Phe
65                  70                  75                  80

Ala Cys Val Ala Ser Thr Leu Ala Trp Asp Arg Gly Tyr Gly Thr Ser
                85                  90                  95

Leu Leu Gly Gly Ser Val Gly Tyr Pro Tyr Gly Gly Ser Gly Phe Gly
            100                 105                 110
```

```
Ser Tyr Gly Ser Gly Tyr Gly Tyr Gly Tyr Gly Tyr
    115                 120             125

Gly Gly Tyr Thr Asp Pro Arg Ala Ala Lys Gly Phe Met Leu Ala Met
130                 135                 140

Ala Ala Phe Cys Phe Ile Ala Ala Leu Val Ile Phe Val Thr Ser Val
145                 150                 155                 160

Ile Arg Ser Glu Met Ser Arg Thr Arg Arg Tyr Tyr Leu Ser Val Ile
                165                 170                 175

Ile Val Ser Ala Ile Leu Gly Ile Met Val Phe Ile Ala Thr Ile Val
                180                 185                 190

Tyr Ile Met Gly Val Asn Pro Thr Ala Gln Ser Ser Gly Ser Leu Tyr
            195                 200                 205

Gly Ser Gln Ile Tyr Ala Leu Cys Asn Gln Phe Tyr Thr Pro Ala Ala
        210                 215                 220

Thr Gly Leu Tyr Val Asp Gln Tyr Leu Tyr His Tyr Cys Val Val Asp
225                 230                 235                 240

Pro Gln Glu Ala Ile Ala Ile Val Leu Gly Phe Met Ile Ile Val Ala
                245                 250                 255

Phe Ala Leu Ile Ile Phe Phe Ala Val Lys Thr Arg Arg Lys Met Asp
                260                 265                 270

Arg Tyr Asp Lys Ser Asn Ile Leu Trp Asp Lys Glu His Ile Tyr Asp
            275                 280                 285

Glu Gln Pro Pro Asn Val Glu Trp Val Lys Asn Val Ser Ala Gly
        290                 295                 300

Thr Gln Asp Val Pro Ser Pro Ser Asp Tyr Val Glu Arg Val Asp
305                 310                 315                 320

Ser Pro Met Ala Tyr Ser Ser Asn Gly Lys Val Asn Asp Lys Arg Phe
                325                 330                 335

Tyr Pro Glu Ser Ser Tyr Lys Ser Thr Pro Val Pro Glu Val Val Gln
            340                 345                 350

Glu Leu Pro Leu Thr Ser Pro Val Asp Asp Phe Arg Gln Pro Arg Tyr
        355                 360                 365

Ser Ser Gly Gly Asn Phe Glu Thr Pro Ser Lys Arg Ala Pro Ala Lys
370                 375                 380

Gly Arg Ala Gly Arg Ser Lys Arg Thr Glu Gln Asp His Tyr Glu Thr
385                 390                 395                 400

Asp Tyr Thr Thr Gly Gly Glu Ser Cys Asp Glu Leu Glu Glu Asp Trp
                405                 410                 415

Ile Arg Glu Tyr Pro Pro Ile Thr Ser Asp Gln Gln Arg Gln Leu Tyr
                420                 425                 430

Lys Arg Asn Phe Asp Thr Gly Leu Gln Glu Tyr Lys Ser Leu Gln Ser
            435                 440                 445

Glu Leu Asp Glu Ile Asn Lys Glu Leu Ser Arg Leu Asp Lys Glu Leu
        450                 455                 460

Asp Asp Tyr Arg Glu Glu Ser Glu Glu Tyr Met Ala Ala Ala Asp Glu
465                 470                 475                 480

Tyr Asn Arg Leu Lys Gln Val Lys Gly Ser Ala Asp Tyr Lys Ser Lys
                485                 490                 495

Lys Asn His Cys Lys Gln Leu Lys Ser Lys Leu Ser His Ile Lys Lys
            500                 505                 510

Met Val Gly Asp Tyr Asp Arg Gln Lys Thr
            515                 520
```